United States Patent
Yu et al.

(10) Patent No.: US 6,541,237 B1
(45) Date of Patent: Apr. 1, 2003

(54) A-1,4-GLUCAN LYASE AND ITS USE IN THE PRODUCTION OF 1.5-ANDROFRUCTOSE

(75) Inventors: Shukun Yu, Malmo (SE); Kirsten Bojsen, Allerod (DK); Jan Marcussen, Copenhagen (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/275,608

(22) Filed: Mar. 24, 1999

Related U.S. Application Data

(63) Continuation of application No. 08/836,156, filed as application No. PCT/EP95/02172 on Jun. 6, 1995, now abandoned, application No. 09/275,608, which is a continuation of application No. PCT/EP94/03397, filed on Oct. 15, 1994.

(30) Foreign Application Priority Data

Nov. 3, 1994 (GB) ............................................. 9422157
Apr. 11, 1995 (GB) ............................................. 9507523

(51) Int. Cl.[7] ............................. C12N 9/88; C12N 5/10; C12N 1/21; C12P 21/00; C07K 17/00

(52) U.S. Cl. ...................... 435/232; 435/69.1; 435/325; 435/252.3; 435/201; 536/23.2; 530/350

(58) Field of Search ............................... 435/201, 69.1, 435/232, 325, 320.1, 252.3; 536/23.2; 530/350

(56) References Cited

U.S. PATENT DOCUMENTS 5,695,970 A * 12/1997 Yu et al. ...................... 435/105

FOREIGN PATENT DOCUMENTS

| EP | 0 177 477 | | 4/1986 |
|---|---|---|---|
| FR | 2 617 502 | | 6/1987 |
| FR | 2617502 | * | 1/1989 |
| FR | 8709197 | | 1/1989 |
| JP | 02100684 A | * | 4/1990 |
| WO | WO 94/09122 | * | 4/1994 |
| WO | WO 95/10616 | | 4/1995 |
| WO | WO 95/10618 | | 4/1995 |

OTHER PUBLICATIONS

Yu et al. (a)Biochemica et Biophysica Acta 1156:313–320, 1993.*
Yu et al. (b)Planta 191(1):137–142, 1993.*
Baute et al. Phytochemistry 27(11): 3401–3403, 1988.*
Baute et al. Bull. Soc. Pharma. Bordeaux 128:9–18, 1989.*
Yu S, et al. "Alpha–1,4–glucan lyase, a new class of starch/glycogen–degrading enzyme. II. Subcellular localization and partial amino–acid sequence" Planta. 1993;191(1):137–42, Jul. 3, 1993.*
Yu S, et al. "Alpha–1,4–Glucan lyase, a new class of starch/glycogen degrading enzyme. I. Efficient purification and characterization from red seaweeds" Biochim Biophys Acta. 1993;1244(1):313–320, Mar. 21, 1993.*

Sanger, F., et al. "DNA sequencing with chain–terminating inhibitors" *Proc. Natl. Acad. Sci. USA* vol. 74, No. 12, pp. 5463–5467, Dec. 1977.

Lichtenthaler, F. W., et al. "A convenient access to 1,5–Anhydroketoses" *Tetrahedron Letters* vol. 21, pp. 1429–1432, 1980.

Collinge, D. B., et al. "Gene expression in *Brassica campestris* showing a hypersensitive . . . " *Plant Molecular Biology* vol. 8, pp. 405–414, 1987.

Frohman, M. A., et al. "Rapid production of full–length cDNAs from rare . . . " *Proc. Natl. Acad. Sci USA* vol. 85, pp. 8998–9002, Dec. 1988.

Baute, M. A., et al. "Fungal enzymic activity degrading 1,4–D–Glucans to 1,5–D–Anhydroructose" *Phytochemistry* vol. 27, No. 11, pp. 3401–3403, 1988.

Punt, P. J., et al. "Intracellular and extracellular production of proteins . . . " *Journal of Biotechnology* vol. 17, pp. 19–34, 1991.

Archer, D. B., et al. "Proteolytic degradation of heterologous proteins expressed . . . " *Biotechnology Letter* vol. 14, No. 5, pp. 357–362, May 1992.

Sounders, G. W., "Gel purification of red algal genomic DNA: An expensive and rapid method for the isolation . . . " *J. Phycol* vol. 29, pp. 251–254, 1993.

Yu, S., et al. "–1,4–Glucan lyase, a new class of starch/glycogen degrading . . . " *Biochimica et Biophysica Acta* vol. 1156, pp. 313–320, 1993.

Jorgensen, K., et al. *Original Paper* "Carotenoid scavenging of radicals" *Lebensm Unters Forsch* vol. 196, pp. 423–429, 1993.

Baute et al., "Bioconversions Fongiques Produisant, A Partir De Sucres, Des Composes Pyrontiques Inhabituels A Activite Antibiotique," Bull. Soc. Pharm. Bordeaux, vol. 128, 1989, pp. 9–18.

LeGendre et al., Gel Electrophoresis Purification of Proteins and Peptides by SDS–PAGE, pp. 74–101, 1988.

Pall et al., A series of six compact fungal transformation vectors containing polylinkers with multiple unique restriction sites, Fungal Genetics Newsletter, No. 40, 1993, pp. 59–63.

Langdale et al., Cellular pattern of photosynthetic gene expression in developing maize leaves. Genes & Development, vol. 2, 1988, pp. 106–115.

Pueschel, C.M., "An Expanded Survey Of The Ultrastructure Of Red Algal Pit Plugs," J. Phycol, vol. 25, 1989, pp. 625–636.

Dellaporta et al., "A plant DNA Minipreparation: Version II," Plant Molecular Biology Reporter, vol. 1, No. 4, pp. 19–21 1983.

(List continued on next page.)

Primary Examiner—Rebecca E. Prouty
Assistant Examiner—Delia Ramirez
(74) Attorney, Agent, or Firm—Nixon & Vanderhye

(57) ABSTRACT

A method of preparing 1,5-D-anhydrofructose in large quantities includes treating α-1,4-glucan with a substantially pure α-1,4-glucan lyase, which has been isolated from algae alone, wherein 1,5-D-anhydrofructose is produced directly from the α-1,4-glucan.

7 Claims, 2 Drawing Sheets

OTHER PUBLICATIONS

Buxton et al., "Transformation of *Asperigillus niger* using the argB gene of *Aspergillus nidulans*," Gene, vol. 37, pp. 207–214, 1985.

Daboussi et al., "Transformation of seven species of filamentous fungi using the nitrate . . . " Current Genetics, vol. 15, pp. 453–456, 1989.

Punt, et al., "Transformation of Filamentous fungi based on Hygromycin B and Phleomycin . . . " Methods of Enzymology, vol. 216, pp. 447–457, 1992.

Baute, et al., Phytochemistry, 27, 3401–3403.

Shukun Yu et al., *a–1,4–Glucan lyase, a new class of starch/glycogen degrading enzyme. I. Efficient purification and characterization from red seaweeds*, Biochimica et Biophysica Acta, vol. 1156, No. 3, 1993, pp. 313–320.

Shukun Yu et al., *a–1,4–Glucan lyase, a new class of starch/glycogen–degrading enzyme. II. Subcellular localization and partial amino–acid sequence*, Planta, vol. 191, 1993, pp. 137–143.

Kevin Jergensen et al., *Original paper, Carotenoid scavenging of radicals*, Lebensmittel–Untersuchung und–Forschung, vol. 196, 1993, pp. 423–429.

Gary W. Saunders, *Gel Purification of Red Algal Genomic DNA: An Inexpensive and Rapid Method for the Isolation of Polymerase Chain Reaction–Friendly DNA*, J. Phycol. vol. 29, 1993, pp. 251–254.

David B. Archer et al., *Proteolytic Degradation of Heterologous Proteins Expressed in Aspergillus niger*, Biotechnology Letters, vol. 14, No. 5, May 1992, pp. 357–361.

Marie–Antoinette Baute et al., *Fungal Enzymic Activity Degrading 1,4–a–D–Glucans to 1,5–D–Anhydrofructose*, Phytochemistry, vol. 27, No. 11, 1988, pp. 3401–3403.

Michael A. Frohman et al., *Rapid production of full–length cDNAs from rare transcripts: Amplification using a single gene–specific oligonucleotide primer*, Proc. Natl'. Acad. Sci. USA, vol. 85, Dec. 1988, pp. 8998–9002.

David B. Collinge et al., *Gene expression in Brassica campestris showing a hypersensitive response to the incompatible pathogen Xanthomonas campestris pv. vitians*, Plant Molecular Biology, vol. 8, 1987, pp. 405–414.

F. W. Lichtenthaler et al., *A Convenient Access to 1,5–Anhydroketoses*, Tetrahedron Letters, vol. 21, 1980, pp. 1429–1433.

F. Sanger et al., *DNA sequencing with chain–terminating inhibitors*, Proc. Natl. Acad. Sci. USA, vol. 74, No. 12, Dec. 1977, pp. 5463–5467.

* cited by examiner

A-1,4-GLUCAN LYASE AND ITS USE IN THE PRODUCTION OF 1.5-ANDROFRUCTOSE

RELATED APPLICATIONS

This application is a Continuation application of application Ser. No. 08/836,156, filed Apr. 15, 1997 now abandoned, which is the U.S. National Phase under 35 U.S.C. § 371 of International Application No. PCT/EP95/02172, filed Jun. 6, 1995; and is a continuation under 35 U.S.C. §365 to Application No. PCT/EP94/03397, filed Oct. 15, 1994, which claims the benefit of priority under 35 U.S.C. §119 to Application No. 9422157.9, filed Nov. 3, 1994 in the United Kingdom, and Application No. 9507523.0, filed Apr. 11, 1995 in the United Kingdom.

BACKGROUND OF THE INVENTION

The present invention relates to an enzyme α-1,4-glucan lyase ("GL") and, in particular, its use to prepare 1,5-D-anhydrofructose ("AF") from substrates based on α-1,4-glucan.

The present invention also relates to the use of a sugar, in particular 1,5-D-anhydrofructose ("AF") prepared by the method of the present invention, as an anti-oxidant, in particular as an anti-oxidant for food stuffs and beverages.

The present invention relates to the use of 1,5-D-anhydrofructose ("AF"), in particular AF prepared by the method of the present invention, as a sweetener, in particular as a sweetener for foodstuffs and beverages, preferably human foodstuffs and beverages.

FR-A-2617502 and Baute et al in Phytochemistry [1988] vol. 27 No.11 pp3401–3403 report on the production of AF in *Morchella vulgaris* by an apparent enzymatic reaction. The yield of production of AF is quite low. Despite a reference to a possible enzymatic reaction, neither of these two documents presents any amino acid sequence data for any enzyme let alone any nucleotide sequence information. These documents say that AF can be a precursor for the preparation of the antibiotic pyrone microthecin.

Yu et al in Biochimica et Biophysica Acta [1993] vol 1156 pp313–320 report on the preparation of GL from red seaweed and its use to degrade α-1,4-glucan to produce AF. The yield of production of AF is quite low. Despite a reference to the enzyme GL this document does not present any amino acid sequence data for that enzyme let alone any nucleotide sequence information coding for the same.

A typical α-1,4-glucan based substrate is starch. Today, starches have found wide uses in industry mainly because they are cheap raw materials.

Starch degrading enzymes can be grouped into various categories. The starch hydrolases produce glucose or glucose-oligomers. A second group of starch degrading enzymes are phosphorylases that produce glucose-1-phosphate from starch in the presence of inorganic phosphate.

SUMMARY OF THE INVENTION

AF has also been chemically synthesised—see the work of Lichtenthaler in Tetrahedron Letters Vol 21 pp 1429–1432. However, this chemical synthesis involves a large number of steps and does not yield large quantities of AF.

The chemical synthetic route for producing AF is therefore very expensive.

There is therefore a need for a process that can prepare AF in a cheap and easy manner and also in a way that enables large quantities of AF to be made.

Furthermore, anti-oxidants are typically used to prevent oxygen having any deleterious effect on a substance such as a foodstuff. Two commonly used anti-oxidants are GRINDOX 142 (antioxidant) and GRINDOX 1029 (antioxidant). These anti-oxidants contain many components and are quite expensive to make.

There is therefore a need to have a simpler and cheaper form of anti-oxidant.

Furthermore, sweeteners are often used in the preparation of foodstuffs and beverages. However, many sweeteners are expensive and complex to prepare.

There is therefore a need to have a simpler and cheaper form of sweetener.

According to a first aspect of the present invention there is provided an enzyme comprising at least any one of the amino acid sequences shown as SEQ. ID. No.s 3–4, or any variant thereof.

According to a second aspect of the present invention there is provided a nucleotide sequence coding for the enzyme of the first aspect of the present invention.

Preferably the nucleotide sequence is a DNA sequence.

According to a third aspect of the present invention there is provided a nucleotide sequence comprising a sequence that is the same as, or is complementary to, or has substantial homology with, or contains any suitable codon substitutions for any of those of SEQ. ID. No. 1 or SEQ. ID. No. 2.

According to a fourth aspect of the present invention there is provided a method of preparing the sugar 1,5-D-anhydrofructose comprising treating an α-1,4-glucan with the enzyme α-1,4-glucan lyase, characterised in that enzyme is used in substantially pure form and wherein the enzyme is isolated from algae alone.

According to a fifth aspect of the present invention there is provided a method of preparing the sugar 1,5-D-anhydrofructose comprising treating an α-1,4-glucan with the enzyme α-1,4-glucan lyase characterised in that enzyme comprises at least any one of the amino acid sequences shown as SEQ. ID. No.s 3–4, or any variant thereof.

According to a sixth aspect of the present invention there is provided the sugar 1,5-D-anhydrofructose when prepared by the method of the present invention.

According to a seventh aspect of the present invention there is provided the use of a reagent that can increase the hydrophobicity of the reaction medium to increase the stability and activity of the GL enzyme.

According to an eighth aspect of the present invention there is provided the use of AF prepared by the method of the present invention as an anti-oxidant.

According to a ninth aspect of the present invention there is provided the use of AF prepared by the method of the present invention as a sweetener.

Preferably the enzyme is obtainable from algae, preferably it is obtainable from *Gracilariopsis lemaneiformis*.

Preferably the enzyme comprises at least any one of the amino acid sequences shown as SEQ. ID. No.s 3–4, or any variant thereof.

Preferably the enzyme is obtained from the expression of a nucleotide sequence coding for the enzyme.

Preferably the nucleotide sequence is a DNA sequence.

Preferably the DNA sequence comprises a sequence that is the same as, or is complementary to, or has substantial homology with, or contains any suitable codon substitutions for any of those of SEQ. ID. No. 1 or SEQ. ID. No. 2.

Preferably if the glucan contains links other than and in addition to the α-1,4- links the α-1,4-glucan lyase is used in conjunction with a suitable reagent that can break the other links.

Preferably the glucan is starch.

Preferably a glucanohydrolase is used in conjunction with the α-1,4-glucan lyase.

Preferably the starch is used in high concentration—such as up to about 25% solution.

Preferably the hydrolase is at least one of pullanase or isoamylase.

Preferably the α-1,4-glucan lyase is bound to a support or, more preferably, is in a dissolved form.

Preferably the enzyme is isolated and/or further purified from algae alone using a gel that is not degraded by the enzyme.

Preferably the gel is based on dextrin or derivatives thereof, preferably the gel is a cyclodextrin—more preferably β-cyclodextrin.

Preferably the substrate is treated with the enzyme in the presence of a buffer.

Alternatively, preferably the substrate is treated with the enzyme in the presence of at least substantially pure water.

Preferably the substrate is treated with the enzyme in the absence of a co-factor.

Preferably the enzyme is used in combination with amylopectin or dextrin.

DETAILED DESCRIPTION OF THE PREFERRED EMBODIMENT

Figure 1A:
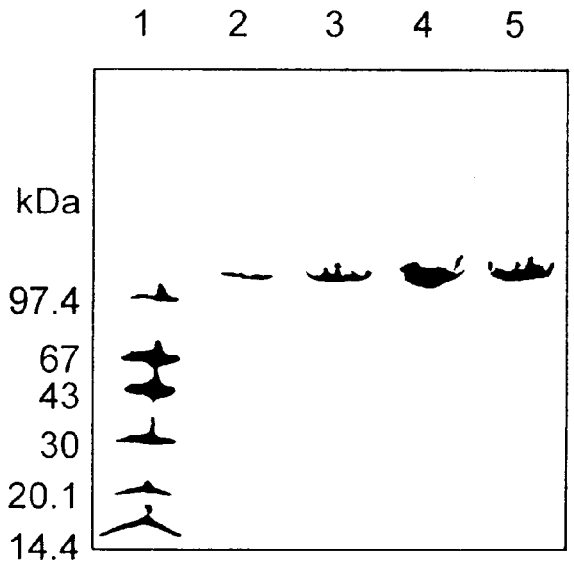
FIG. 1A is the result of electrophoresis of algal α-1,4-glucan lyases using SDS-PAGE on 8–25% gradient gels, according to the present invention.

The terms "variant" or "homologue" include any substitution of, variation of, modification of, replacement of, deletion of or addition of one (or more) nucleic acid or amino acid from or to the respective sequence providing the resultant sequence has the respective ability to code for or act as an enzyme according to the present invention. In particular, the term "homologue" covers homology with respect to structure and/or function providing the resultant nucleotide sequence has the ability to act as a promoter. With respect to sequence homology, preferably there is more than 80% homology, more preferably at least 85% homology, more preferably at least 90% homology, even more preferably at least 95% homology, more preferably at least 98% homology. Thus, the expression "substantial homology" covers homology with respect to structure and/or nucleotide components and/or biological activity.

The expression "contains any suitable codon substitutions" covers any codon replacement or substitution with another codon coding for the same amino acid or any addition or removal thereof providing the resultant enzyme has lyase activity.

In other words, the present invention also covers a modified DNA sequence in which at least one nucleotide has been deleted, substituted or modified or in which at least one additional nucleotide has been inserted so as to encode a polypeptide having the activity of a glucan lyase, preferably having an increased lyase activity.

AF prepared by the present method was confirmed and characterised by $^{13}C$ NMR.

One of key advantages of the present method is that the sugar 1,5-D-anhydrofructose can be prepared in much larger quantities than before and by a method that is relatively easier and cheaper than the known processes. For example the sugar can now be prepared in amounts of for example greater than 100 g—such as 500 g—compared to the prior art methods when only much smaller amounts were and could be produced—such as micro gram amounts.

Typical reactions that can be catalyzed by GL can be summarised as follows:

1). Amylopectin - - - → AF+limit dextrin
2). Amylose - - - → AF+limit dextrin
3). Dextrin - - - → AF+glucose In reaction 1), the ratio of the two products depend on the structure of amylopectin or the distribution of α-1,6-glucosidic linkages in the amylopectin molecules.

In reaction 2) and 3), the ratio of the products depends on the degree of polymerisation (DP) number of the substrate. In reaction 3 the ratio between AF and glucose depends upon the DP. For example if the dextrin contains 10 glucose units the ratio AF:glucose would be 9:1.

Another advantage of the present invention is that glucans that contain links other than α-1,4- links can be substantially degraded—whereas before only partial degradation was achieved. The substantial degradation of the 1,5-D-anhydrofructose precursor is one of the factors leading to the increased yields of 1,5-D-anhydrofructose.

Another advantage is that AF is a naturally occurring substance and therefore it has a potential for human purposes. For example, it can be converted to the antibiotic microthecin by AF dehydrase. Antibiotics are known for their uses in food bio-preservation, which is an important area in food technology. However, to date, the preparation of AF and also microthecin has had a number of disadvantages. For example, only small quantities could be produced. Also, the process was costly.

The present invention overcomes these problems by providing a larger production of and much cheaper production of AF and so also other products such as microthecin. In this regard, it is possible to prepare gram to kilogram amounts of AF.

A further advanatge is that the lyase is stable for at least one year at 4° C. and can be lyophilized without loss of activity.

Another advantage is that the lyase produces AF directly from starches and does not need the presence of any co-factors.

Another advantage is that the enzyme can be used in pure water. This result is very surprising.

Based on the simple properties of the present lyase, one can expect that the production cost of AF will be comparable to that of glucose. This is especially advantageous that the present lyase does not necessarily require the presence of any co-factors which are generally very expensive.

In general α-1,4-glucans can be used as substrate for the enzyme.

As a preferred substrate, starch is used.

In a preferred process, soluble or gelatinized starch or starch hydrolysate are used. The starch hydrolysates can be prepared either chemically or enzymatically.

If an enzyme is used for the partial starch degradation the enzyme can either be added before the addition of the lyase or any other additional starch degrading reagent (such as the enzyme glucanohydrolase) which may be added simultaneously.

The lyase will convert the glucan to AF. The enzyme will attack the substrate from the non reducing end and leave only the reducing sugar unconverted. The residual glucose can be removed by known methods some of which have been described here.

Using the reaction described here pure AF can be produced and also in large amounts.

Thus, in one embodiment, the α-1,4-glucan lyase is purified from algae—such as *Gracilariopsis lemaneiformis*—by affinity chromatography on β-cyclodextrin Sepharose, ion exchange chromatography on Mono Q HR 5/5 and gel filtration on Superose 12 columns. The purified enzyme produces 1,5-anhydro-D-fructose from α-1,4-glucans.

The enzymes of the present invention convert amylose and amylopectin to 1,5-anhydrofructose.

Among the maltosaccharides tested, we found that the lyase showed low activity towards maltose, and lower activity to maltotriose and maltoheptaose with the highest activity to maltotetraose and maltopentaose. The enzyme showed no substrate inhibition up to a concentration 10 mg ml$^{-1}$ among these maltosaccharides.

The enzymes from the preferred source have been sequenced and the amino acid sequences are presented later.

Also presented later are the DNA sequences coding for the enzymes.

The present invention therefore describes a new starch degrading enzyme—namely a new α-1,4-glucan lyase. This is an enzyme that has been purified and characterized for the first time.

As mentioned above, the present invention also relates to some specific uses of AF. In particular, the present invention relates to the use of 1,5-D-anhydrofructose ("AF"), as an anti-oxidant, in particular as an anti-oxidant for food stuffs and beverages.

Therefore according to the present invention there is provided the use of 1,5-D-anhydrofructose (AF) as an anti-oxidant.

Preferably AF is or is used in an edible substance.

Preferably AF is used in or as a foodstuff or beverage.

Preferably, AF is used in combination with another anti-oxidant.

Preferably the AF is prepared by the method according to the present invention.

The main advantages of using AF as an anti-oxidant are that it is a natural product, it is likely that it is non-metabolisable at least for humans, it is easy to manufacture, it is water-soluble, and it is generally non-toxic.

A preferred embodiment the present invention therefore relates to the enzymatic preparation of pure AF which can be used as an attractive water soluble antioxidant for food and non-food purposes. Examples are given below for the use of AF as an antioxidant in food formulations.

Experiments showed that the AF is comparable with known high quality commercial available food antioxidants.

Non-food examples include use in polymer chemistry as oxygen scavengers during the synthesis of polymers.

Also, AF could be used for the synthesis of biodegradable plastic.

Experiments have shown that AF can be an efficient reducing agent (antioxidant), as it can easily reduce 3,5-dinitrosalicylic acid to 3-amino-5-nitrosalicylic acid.

AF is a naturally occurring substance and therefore it has a tremendous potential for use as an acceptable antioxidant. AF can also be converted into the antibiotic microthecin by AF dehydrase. Antibiotics are known for their uses in food biopreservation, an important area in food biotechnology.

In another aspect, the present invention also relates to the use of 1,5-D-anhydrofructose as a sweetener, in particular as a sweetener for foodstuffs and beverages, preferably human foodstuffs and beverages.

Thus according to this aspect of the present invention there is provided the use of 1,5-D-anhydrofructose as a sweetener.

Preferably the AF is used as or in a human foodstuff or beverage.

The AF may be used in any desired amount such as a 5% solution or 100 mg/kg to 500 mg/kg.

The advantages of using AF as a sweetener are that it is a natural product, it is generally non-toxic, it is water soluble, it is likely that it is non-metabolisable at least for humans, and it is easy to manufacture.

The present invention therefore also relates to a novel application of AF as a sweetener.

Preferably the AF is prepared by the method according to the present invention.

Further aspects of the present invention include:

a method of preparing the enzyme α-1,4-glucan lyase (GL) comprising isolating the enzyme from algae alone;

a nucleotide sequence coding for the enzyme α-1,4-glucan lyase, preferably wherein the sequence is not in its natural environment (i.e. it does not form part of the natural genome of a cellular organism capable of expressing the enzyme, preferably wherein the nucleotide sequence is a DNA sequence;

the use of β-cyclodextrin to purify an enzyme, preferably GL.

Other preferred embodiments of the present invention include any one of the following: A transformed cell, tissue, organ or host organism having the capability of producing AF as a consequence of the introduction of a DNA sequence as herein described; such a transformed host organism which is a microorganism—preferably wherein the host organism is selected from the group consisting of bacteria; moulds; fungi and yeast; preferably the cell, tissue, organ or host organism is obtained from or is any one of the group consisting of Saccharomyces, Kluyveromyces, Aspergillus, Trichoderma Hansenula, Pichia, Bacillus Streptomyces, Eschericia such as *Aspergillus oryzae, Saccharomyces cerevisiae, bacillus sublilis, Bacillus amyloliquefascien, Eschericia coli.*; A method for preparing the sugar 1,5-D-anhydrofructose comprising the use of a transformed host organism expressing a nucleotide sequence encoding the enzyme α-1,4-glucan lyase, preferably wherein the nucleotide sequence is a DNA sequence, preferably wherein the DNA sequence is one of the sequences hereinbefore described; A vector incorporating a nucleotide sequence as hereinbefore described, preferably wherein the vector is a replication vector, preferably wherein the vector is an expression vector containing the nucleotide sequence downstream from a promoter sequence, preferably the vector includes a marker (such as a resistance marker); Cellular organisms, or cell line, transformed with such a vector; A method of producing the product α-1,4-glucan lyase or any nucleotide sequence or part thereof coding for same, which comprises culturing such an organism (or cells from a cell line) transfected with such a vector and recovering the product.

In particular, in the expression systems, the enzyme should preferably be secreted to ease its purification. To do so the DNA encoding the mature enzyme is fused to a signal sequence, a promoter and a terminator from the chosen host.

For expression in *Aspergillus niger* the gpdA (from the Glyceraldehyde-3-phosphate dehydrogenase gene of Aspergillus nidulans) promoter and signal sequence is fused to the 5' end of the DNA encoding the mature lyase. The terminator sequence from the A. niger trpC gene is placed 3' to the gene (Punt, P. J. et al 1991—(1991): J. Biotech. 17, 19–34). This construction is inserted into a vector containing a replication origin and selection origin for E. coli and a selection marker for A. niger. Examples of selection markers for A. niger are the amdS gene, the argB gene, the pyrG gene, the hygB gene, the BmlR gene which all have been used for selection of transformants. This plasmid can be transformed into A. niger and the mature lyase can be recovered from the culture medium of the transformants. Eventually the construction could be transformed into a protease deficient strain to reduce the proteolytic degradation of the lyase in the culture medium (Archer D. B. et al 1992—Biotechnol. Lett. 14, 357–362).

Instead of Aspergillus niger as a host, other industrial important microorganisms for which good expression systems are known could be used such as: Aspergillus oryzae, Aspergillus sp., Trichoderma sp., Saccharomyces cercvisiae, Kluyveromyces sp., Hansenula sp., Pichia sp., Bacillus subtilis, B. amyloliquefaciens, Bacillus sp., Streptomyces sp. or E. coli. Also, other forms of algae may be used.

The following sample was accepted as a deposit in accordance with the Budapest Treaty at the recognised depositary The Culture Collection of Algae and Protozoa (CCAP) at Dunstaffnage Marine Laboratory PO Box 3, Oban, Argyll, Scotland, United Kingdom, PA34 4AD on Oct. 11, 1994:

Gracilariopsis lemaneiformis (CCAP 1373/2)—[ref. GISC-1 (California)].

Thus a highly preferred embodiment of the present invention includes a GL enzyme or a nucleotide sequence coding for same obtainable from the algae that is the subject of deposit CCAP 1373/2.

Figure 1B:
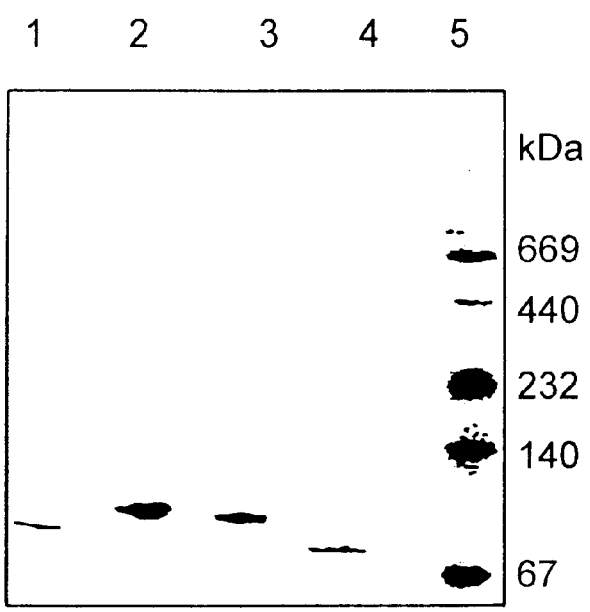
FIG. 1B is the result of electrophoresis of algal α-1,4-glucan lyases using Native-PAGE on 8–25% gradient gels, according to the present invention.
Figure 2:
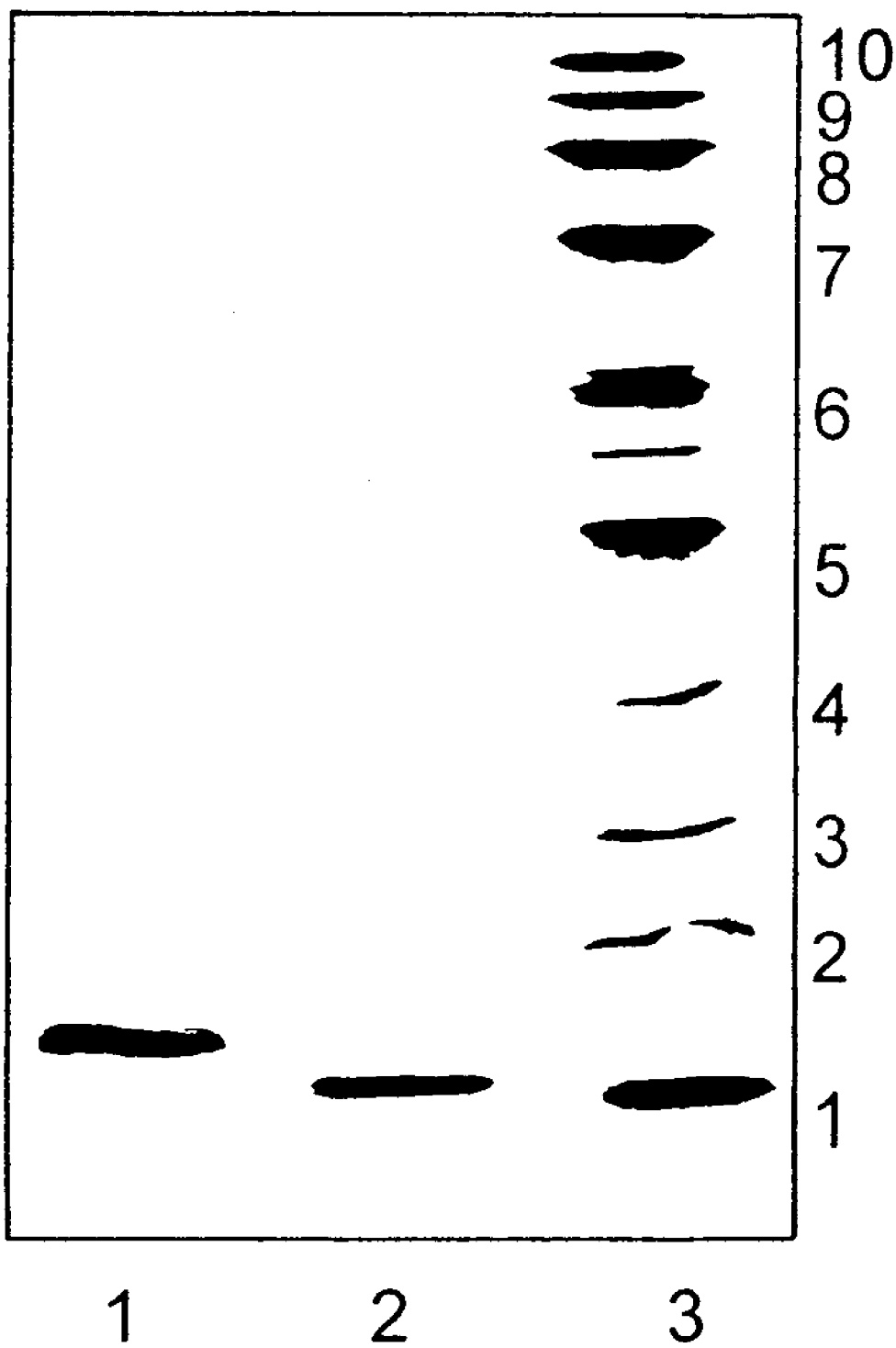
FIG. 2 is the result of isoelectric focusing of the α-1,4-glucan lyases on a gel with a pH gradient of pH 3 to pH 9, according to the present invention.

The present invention will now be described only by way of example, in which reference shall be made to Figures which shows the results of some electrophoretic studies on algal α-1,4-glucan lyases, and FIG. 2 which shows the results of some isoelectric focus studies on α-1,4-glucan lyases on a gel with a pH gradient of pH 3 to pH 9. FIGS. 1 and 2 are are described in more detail later.

PREPARATION OF α-1,4-GLUCAN LYASE

The enzyme α-1,4-glucan lyase according to the present invention (e.g. for use in preparing AF) may be isolated from algae alone, preferably Gracilariopsis lemaneiformis, more preferably Gracilariopsis lemaneiformis from Santa Cruz, (Calif.).

The initial enzyme purification can be performed by the method as described by Yu et al (ibid). However, preferably, the initial enzyme purification includes an optimized procedure in which a solid support is used that does not decompose under the purification step. This gel support further has the advantage that it is compatible with standard laboratory protein purification equipment. The details of this optimized purification strategy are given later on. The purification is terminated by known standard techniques for protein purification. The purity of the enzyme can be readily established using complementary electrophoretic techniques.

CHARACTERISATION OF THE ENZYME

Amino acid sequence analysis

The α-1,4-glucan lyase from Gracilariopsis lemaneiformis was digested with either endoproteinase Arg-C from Clostridium histolyticum or endoproteinase Lys-C from Lysobacter enzymogenes, both sequencing grade purchased from Boehringer Mannheim, Germany. For digestion with endoproteinase Arg-C, freeze dried lyase (0.1 mg) was dissolved in 50 μl 10 M urea, 50 mM methylamine, 0.1 M Tris-HCl, pH 7.6. After overlay with $N_2$ and addition of 10 μl of 50 mM DTT and 5 mM EDTA the protein was denatured and reduced for 10 min at 50° C. under $N_2$. Subsequently, 1 μg of endoproteinase Arg-C in 10 μl of 50 mM Tris-HCl, pH 8.0 was added, $N_2$ was overlayed and the digestion was carried out for 6 h at 37° C. For subsequent cysteine derivatization, 12.5 μl 100 mM iodoacetamide was added and the solution was incubated for 15 min at RT in the dark under $N_2$.

For digestion with endoproteinase Lys-C, freeze dried lyase (0.1 mg) was dissolved in 50 μl of 8 M urea, 0.4 M $NH_4HCO_3$, pH 8.4. After overlay with $N_2$ and addition of 5 μl of 45 mM DTT, the protein was denatured and reduced for 15 min at 50° C. under $N_2$. After cooling to RT, 5 μl of 100 mM iodoacetamide was added for the cysteines to be derivatized for 15 min at RT in the dark under $N_2$.

Subsequently, 90 μl of water and 5 μg of endoproteinase Lys-C in 50 μl of 50 mM tricine and 10 mM EDTA, pH 8.0, was added and the digestion was carried out for 24 h at 37° C. under $N_2$.

The resulting peptides were separated by reversed phase HPLC on a VYDAC C18 column (0.46×15 cm; 10 μm; The Separations Group; California) using solvent A: 0.1% TFA in water and solvent B: 0.1% TFA in acetonitrile. Selected peptides were rechromatographed on a Develosil C18 column (0.46×10 cm; 3 μm; Dr. Ole Schou, Novo Nordisk, Denmark) using the same solvent system prior to sequencing on an Applied Biosystems 476A sequencer using pulsed-liquid fast cycles.

The amino acid sequence information from the enzyme derived from Gracilariopsis lemaneiformis is shown below (corresponds to SEQ. ID. No. 3) where the sequenced peptides are underlined.

```
MFPTLTFIAP  SALAASTFVG  ADIRSGIRIQ  SALPAVRNAV  RRSKHYNVSM  TALSDKQTAI

SIGPDNPDGI  NYQNYDYIPV  AGFTPLSNTN  WYAAGSSTPG  GITDWTATMN  VKFDRIDNPS

YSNNHPVQIQ  VTSYNNNSFR  IRFNPDGPIR  DVSRGPILKQ  QLTWIRNQEL  AQGCNPNMSF

SPEGFLSFET  KDLNVIIYGN  CKMRVTKKDG  YLVMENDECN  SQSDGNKCRG  LMYVDRLYGN

AIASVQTNFH  KDTSRNEKFY  GAGEVNCRYE  EQGKAPTYVL  ERSGLAMTNY  NYDNLNYNQP

DVVPPGYPDH  PNYYIPMYYA  APWLVVQGCA  GTSKQYSYGW  FMDNVSQSYM  NTGDTAWNCG

QENLAYMGAQ  YGPFDQHFVY  GDGDGLEDVV  KAFSFLQGKE  FEDKKLNKRS  VMPPKYVFGF
```

```
                               -continued
FQGVFGALSL  LKQNLPAGEN  NISVQEIVEG  YQDNDYPFEG  LAVDVDMQDD  LRVFTTKPEY

WSANMVGEGG  DPNNRSVFEW  AHDRGLVCQT  NVTCFLRNDN  SGKPYEVNQT  LREKQLYTKN

DSLNNTDFGT  TSDGPGDAYI  GHLDYGGGVE  CDAIFPDWGR  PDVAQWWGEN  YKKLFSIGLD

FVWQDMTVPA  MMPHRLGDAV  NKNSGSSAPG  WPNENDPSNG  RYNWKSYHPQ  VLVTDMRYGA

EYGREPMVSQ  RNIHAYTLCE  STRREGIVGN  ADSLTKFRRS  YIISRGGYIG  NQHFGGMWVG

DNSATESYLQ  MMLANIINMN  MSCLPLVGSD  IGGFTQYNDV  GDPTPEDLMV  RFVQAGCLLP

WFRNHYDRWI  ESKKHGKKYQ  ELYMYPGQKD  TLKKFVEFRY  RWQEVLYTAM  YQNATTGEPI

IKAAPMYNND  VNVYKSQNDH  FLLGGHDGYR  ILCAPVVREN  ATSREVYLPV  YSKWFKFGPD

FDTKPLENEI  QGGQTLYNYA  APLNDSPIFV  REGTILPTRY  TLDGVNKSIN  TYTDNDPLVF

ELFPLENNQA  HGLFYHDDGG  VTTNAEDFGK  YSVISVKAAQ  EGSQMSVKFD  NEVYEHQWGA

SFYVRVRNMG  APSNINVSSQ  IGQQDMQQSS  VSSRAQMFTS  ANDGEYWVDQ  STNSLWLKLP

GAVIQDAAIT  VR
```

In addition, for the characterization of α-1,4-glucan lyase from a red seaweed *Gracilariopsis lemaneiformis* collected in Santa Cruz, Calif. and apparently not infected by fungi, the following amino acid composition of the lyase was found:

| Amino acid residues | mol % of each residue |
|---|---|
| Asx | 15.42 |
| Thr | 5.24 |
| Ser | 6.85 |
| Glx | 9.46 |
| Pro | 5.46 |
| Gly | 9.08 |
| Ala | 5.38 |
| ½Cys | 1.57 |
| Val | 6.60 |
| Met | 2.90 |
| Ile | 3.66 |
| Leu | 6.00 |
| Tyr | 6.00 |
| Phe | 4.37 |
| His | 1.65 |
| Lys | 4.44 |
| Arg | 4.17 |
| Trp | 1.75 |
| Total: | 100.00 |

Comparing the peptide sequences from the Californian algae with the amino acid sequence from a fungally infected algae from China (described in co-pending PCT patent application No. PCT/EP/0339) showed a high degree of homology (72–79% identity between the amino acid sequence in SEQ. ID. No. 3 and No. 4 generated from the PCR fragments and the corresponding sequences in the GL obtained from the algae from China) between the protein sequences.

The alignment of the protein sequences showed that sequence position 1 to 50 of SEQ. ID. No. 3 represents a signal sequence and sequence position 51 to 1092 represents the mature protein.

SEQ. I.D. No.3 has the following characteristics:

Number of residues: 1092

Molecular weight (MW): 123169

Amino acid composition (including the signal sequence):

| | | | |
|---|---|---|---|
| 64 Ala | 14 Cys | 18 His | 33 Met |
| 56 Thr | 48 Arg | 55 Gln | 45 Ile |
| 49 Phe | 22 Trp | 89 Asn | 49 Glu |
| 65 Leu | 59 Pro | 67 Tyr | 73 Asp |
| 94 Gly | 46 Lys | 73 Ser | 73 Val |

SEQ. ID. No. 4 is a partial sequence corresponding to amino acid 287 to 861 in SEQ. ID. No. 3. The identity between the two sequences is 81%.

DNA sequence analysis

DNA from *Gracilariopsis lemaneiformis* was isolated as described by Saunders (1993) with the following modification: The polysaccharides were removed from the DNA by ELUTIP-d (Schleicher & Schuell) purification instead of gel purification. (Ref: Saunders, G. W. (1993). Gel purification of red algal genomic DNA: An inexpensive and rapid method for the isolation of PCR-friendly DNA. Journal of phycology 29(2): 251–254 and Schleicher & Schuell: ELUTIP-d. Rapid Method for Purification and Concentration of DNA.)

For PCR, the appropriate DNA molecule was prepared by use of the Gene Amp DNA Amplification Kit (Perkin Elmer Cetus, USA) and in accordance with the manufactures instructions except that the Taq polymerase was added later (see PCR cycles) and the temperature cycling was changed to the following:

| PCR cycles: no of cycles | C | time (min.) |
|---|---|---|
| 1 | 98 | 5 |
|  | 60 | 5 |
| addition of Taq polymerase and oil | | |
| 35 | 94 | 1 |
|  | 47 | 2 |
|  | 72 | 3 |
| 1 | 72 | 20 |

PCR fragments were cloned into pT7Blue (from Novagen) or Script™SK(+) following the instructions of the supplier.

The double stranded DNA was sequenced essentially according to the dideoxy method of Sanger et al. (1979) using the Auto Read Sequencing Kit (Pharmacia) and the Pharmacia LKB A.L.F.DNA sequencer. (Ref: Sanger, F., Nicklen, S. and Coulson, A.R.(1979). DNA sequencing with chain-determinating inhibitors. Proc. Natl. Acad. Sci. USA 74: 5463–5467.). The sequences are shown as SEQ. ID. No.s 1–2.

For the initial PCR, the following three oligonucleotide sequences were generated from two peptide sequences from the Californian algae to generate a PCR fragment of app. 970 bp.

Primer 1 (SEQ ID NO:5): ATGAC(GATC)AA(CT)TA(CT) AA(CT)TA(CT)GA(CT)AA

Primer 2 (SEQ ID NO:6): (AG)TG(GATC)GGCATCAT (GATC)GC(GATC)GG(GATC)AC

Primer 3 (SEQ ID NO:7): GTCAT(GA)TC(CT)TGCCA (GATC)AC(GA)AA(GA)TC

Primer 1 corresponds to the codons for amino acids 287–293 in SEQ. I.D. No. 3.

Primer 2 and primer 3 correspond to codons (of the complementary strands) for amino acids 608–614 and 599–607 of SEQ. ID. No. 3, respectively.

Primer 1 was used as the upstream primer and primer 2 was used as the downstream primer in the first PCR amplification. In the second PCR amplification primer 1 was used as the upstream primer and primer 3 was used as the downstream primer. A PCR fragment of the expected size was generated and cloned into the pT7blue vector from Novagen. Two independent plasmids containing a PCR fragment were sequenced and it was seen that those two cloned PCR fragments contained the codons for peptide sequences originating from two different proteins. This indicates that there are at least two different genes coding for α-1,4-glucan lyase in the Californian algae containing sequences shown as SEQ. ID. No.s 1–2—their putative amino acid sequences are shown as SEQ. ID. No.s 3–4.

Further PCR using the Pfu polymerase from Stratagene were made according to the manufactures instruction using the same temperature cycling as for the Taq polymerase. The PCR fragments were cloned into either the pT7Blue plasmid from Novagen or the pCR-Script™ SK(+) plasmid from Stratagene.

Four additional PCR amplifications were performed using the following primers.

For the first PCR the primer
GA(CT) AA(CT) CC(GATC) GA(CT) GG(GATC) AT(ATC) (GA)A(CT) TA (SEQ ID NO:8)
corresponding to codons for amino acids 65–72 of SEQ. ID. No.3 was used as the upstream primer and the primer
(GA)GA (TG)AC ATT (GA)TC CA(AT) AAA CCA (SEQ ID NO:9)
generated from the initial PCR corresponding to codons (of the complementary strand) for amino acids 340–346 of SEQ. ID. No.3 was used as the downstream primer.

In the second PCR the primer
GT(GA) GAT GT(GT) GAT ATG CAA (GC)A(AT) GA (SEQ ID NO:10)
generated from the initial PCR corresponding to codons for amino acids 463–470 of SEQ. ID. No.3 was used as the upstream primer and the primer
CCA CAT (GATC)CC (GATC)CC (GA)AA (GA)TG (CT) TG (GA)TT (SEQ ID NO:11)
corresponding to codons (of the complementary strand) for amino acids 711–718 of SEQ. ID. No.3 was used as the downstream primer.

In the third PCR the primer
GTG AGT CTA CTA GGA GGG AA (SEQ ID NO:12)
generated from the initial PCR corresponding to codons for amino acids 389–395 of SEQ. I.D.No.4 was used as the upstream primer and the primer
A(GA) (GA)AA (GA)TG (GA)TC (GA)TT (CT)TG (SEQ ID NO:13)
corresponding to codons (of the complementary strand) for amino acids 566–571 of SEQ. ID. No. 4 was used as the downstream primer.

In the fourth PCR the primer
TTC CCA GA(CT) TGG GGT CGA CC (SEQ ID NO:14)
generated from the initial PCR corresponding to codons for amino acids 575–581 of SEQ. ID. No. 3 was used as the upstream primer and the primer
GT(GA) AA(GA) TC(GATC) GG(GATC) CC(GA) AA (SEQ ID NO:15)
corresponding to codons (of the complementary strand) for amino acids 897–902 of SEQ. ID. No. 3 was used as the downstream primer.

The first PCR amplification generated a DNA sequence corresponding to nucleotides 193–1038 in SEQ. ID. No. 1.

The second PCR amplification generated DNA sequences corresponding to nucleotides 1387–2154 in SEQ. ID. No. 1 and nucleotides 526–1284 in SEQ. ID. No. 2.

The third PCR amplification generated a DNA sequence corresponding to nucleotides 1165–1712 in SEQ. ID. No. 2.

The fourth PCR amplification generated a DNA sequence corresponding to nucleotides 1723–2706 in SEQ. ID. No. 1.

To obtain the 5' and 3' end of SEQ. ID. No.3 the RACE (rapid amplification of cDNA ends) procedure was performed (Michael, A. F., Michael, K. D. & Martin, G. R. (1988). Proc.Natl.Acad.Sci.USA 85:8998–9002) using the 5'Race system from Gibco BRL for the 5'Race. Total RNA was isloated according to Collinge et al. (Collinge, D. B., Milligan, D. E., Dow, J. M., Scofield, G. & Daniels, M. J.(1987). Plant Mol Biol 8:405–414). The 5'Race was done according to the protocol of the manufacturer, using 1 µg of total RNA and the sequence
GGT AGC GGT CCA GTC GGT GAT GCC (SEQ ID NO:16)
(identical to the complementary strand of nucleotides 301–324 in SEQ. ID. No. 1) as a primer in the first strand synthesis.

The sequence
AGA GCC GGC AGC ATA CCA GTT GGT GTT GG (SEQ ID NO:17)
identical to the complementary strand of nucleotides 260–288 in SEQ. ID. No. 1 was used for the PCR amplification.

In the 3'Race the following primer
GAA GGA TCC GTC GAC ATC GAT AAT ACG ACT GAA TTC GGG ATT TTT TTT TTT TTT TTT (SEQ ID NO:18)
was used for the first strand synthesis.

The gene specific primer
GAC GGC TAT CGT ATT CTC TGC (SEQ ID NO:19)
identical to nucleotides 2599–2619 in SEQ. ID. No. 1 was used in the first PCR amplification, while primer
TAC CTG CCT GTG TAT AGC AAG (SEQ ID NO:20)
corresponding to nucleotides 2659–2679 was used as the gene specific primer in the second PCR amplification.

The sequence
AAG GAT CCG TCG ACA TCG ATA AT (SEQ ID NO:21)
was used as the downstream primer in both PCR amplifications. The GeneAmp RNA PCR kit from Perkin Elmer was used for the 3'Race.

After the 5' and 3' Race the PCR fragments were blunt ended with the Pfu polishing kit from Stratagene before cloning into the pCR Script™ SK(+) plasmid.

BIOCHEMICAL CHARACTERIZATION

Electrophoretic properties of the α-1,4-glucan lyase purified from the red alga *Gracilariopsis lemaneiformis* collected in Santa Cruz, Calif. (USA), as compared with lyases collected in Qingdao (China) and Sucre Pennisula (Venezuella), and with lyases isolated from the fungi *Morchella costata, M. vulgaris*.

Two lyases (GLsc1-lyase and GLsc2-lyase) were purified from the red alga *Gracilariopsis lemaneiformis* collected in Santa Cruz, Calif. (USA), using the procedure developed for the purification of the lyase from the red alga collected from Qingdao China. The two forms were purified to electrophoretic homogeneity (FIGS. 1A and 1B). Partial amino acid sequences were obtained from the purified GLsc1-lyase and were used to generate PCR primers. The molecular mass was estimated to 116 kDa for both GLsc1-lyase and GLsc2-lyase, by the SDS-PAGE method (FIG. 1A).

On the native PAGE (FIG. 1B), GLsc1-lyase and GLsc2-lyase migrated slower than GL1-lyase. On the isoelectrofucsing gel, GLsc1-lyase showed a pI of 4.1 (FIG. 2). A comparison of the relative migration rates and the pI values of the different lyases studied are listed in the following table.

| Enzyme name | Origin | Migration | pI |
|---|---|---|---|
| GL1-lyase | QC | ++++ | 3.8 |
| GLsc1-lyase | SCC | +++ | 4.1 |
| GLsc2-lyase | SCC | +++ | 4.1 |
| GLv-lyase | SpV | +++ | 4.1 |
| MV-lyase | MvA | ++ | 4.4 |
| MC-lyase | McA | + | 4.5 |

CODES:

QC=Qingdao, China

SCC=Santa Cruz, Calif.

SpV=Sucre pennisula, Venezuela

MvA=*Morchella vulgaris,* ATCC

McA=*Morchella costata,* ATCC

The relative migration rates were estimated from native PAGE on gels with 8–25% gradient; the pI values were estimated by isoelectrofocusing on gels with a pH gradient of 3–9. From the table it is seen that the GLq1-lyase exhibited the fastest migration rate on native-PAGE and exhibited the lowest pI values of 3.8 while the MC-lyase showed the slowest migration rate and the highest pI value of 4.5.

The Figures are now discussed in more detail.

FIG. 1. Electrophoresis of algal α-1,4-glucan lyases.

A. SDS-PAGE on 8–25% gradient gels. The gel was stained with PhastGel Blue R.

Lane 1: the molecular markers of phosphorylase b (97.4 kDa); bovine serum albumin (67 kDa), ovalbumin (43 kDa), carbonic anhydrase (30 kDa), soybean trypsin inhibitor (20.1 kDa), and β-lactalbumin (14.4 kDa).

Lane 2: the purified Glq1-lyase from the red alga *Gracilariopsis lemaneiformis* collected in Qingdao (China).

Lanes 3 and 5: the purified GLsc1-lyase from the red alga *Gracilariopsis lemaneiformis* collected in Santa Cruz, Calif. (USA).

Lane 4: the purified GLsc2-lyase from the red alga *Gracilariopsis lemaneiformis* collected in Santa Cruz, Calif. (USA).

B. Native-PAGE on 8–25% gradient gel. The gel was stained with PhastGel Blue R.

Lane 1 and 4: the purified GLq1-lyase from the red alga *Gracilariopsis lemaneiformis* collected in Qingdao (China).

Lane 2: the purified GLsc2-lyase from the red alga *Gracilariopsis lemaneiformis* collected in Santa Cruz, Calif. (USA).

Lane 3: the purified GLsc1-lyase from the red alga *Gracilariopsis lemaneiformis* collected in Santa Cruz, Calif. (USA).

Lane 5: the protein markers: thyroglobulin (669 kDa), ferritin (440 kDa), catalase (232 kDa), lactate dehydrogenase (140 kDa) and albumin (67 kDa).

FIG. 2. Isoelectric focusing of the α-1,4-glucan lyases on a gel with a pH gradient of pH 3 to pH 9. The gel was stained with PhastGel Blue R.

Lane 1: GLsc1-lyase purified from *Gracilariopsis lemaneiformis* collected in Santa Cruz Calif. showing a pI of 4.1.

Lane 2: GLq1-lyase purified from *G. lamaneifromis* collected in Qingdao (China) showing a pI of 3.8.

Lane 3: the pI markers: 1 amyloglucosidase (3.50), 2 soybean trypsin inhibitor (4.55), 3 β-lactoglobumin A (5.20), 4 bovine carbonic anhydrase B (5.85), 5 human carbonic anhydrase B (6.55), 6 horse myoglobin (acidic, 6.85), 7 horse myoglobin (basic 7.35), 8 lentil lectin (acidic 8.15), 9 lentil lectin (middle, 8.45), 10 lentil lectin (baic, 8.65).

Further studies showed that $K_m$ was 3.76 mg/ml for amylopectin and 3.37 mg/ml for glycogen.

| DEGRATION STUDIES | |
|---|---|
| The degradation rates of the lyase on various substrates are given below. | |
| Substrate | AF released (nmol) |
| Maltose | 657 |
| Maltotriose | 654 |
| Maltotetraose | 670 |
| Maltopentaose | 674 |
| Maltohexaose | 826 |
| Maltoheptaose | 865 |
| Dextrin 20 | 775 |
| Dextrin 15 | 775 |
| Dextrin 10 | 844 |
| Amylopectin | 732 |
| Glycogen | 592 |

Reaction conditions: The reaction mixture contained 10 mM of HOAc-NaOAc (pH 3.8). The substrate concentration was 10 mg/ml. The final volume was 100 ul after the addition of lyase and water. The reaction time was 40 min at 45° C.

The lyase was not able to degrade pullulan, nigeran tetrasaccharide, trehalose, isomaltose, glucose, α-, β- and r-cyclodextrins. The lyase degraded panose and nigerose though at a slow rate.

The temperature optimum for the lyase was 48° C. when amylopectin was used as substrate and 50° C. when glycogen was used as substrate. At 50° C., the reactivity of glycogen was similar to that of amylopectin; below 50° C., amylopectin was a better substrate than glycogen.

The pH optimum range for the lyase was between pH 3.5 and pH 7.0; the optimal pH was 3.8. The buffers used in the pH tests were glycine-HCl (pH 2.2–3.6); NaOAc-HOAc (pH 3.5–5.5); Mes-NaOH (pH 5.5–6.7); Mops-NaOH (pH 6.0–8.0) and bicine-NaOH (pH 7.6–9.0). All buffers used were 40 mM.

At a final concentration of 2 mM, p-chloromercuribenzoic acid (PCMB) inhibited the lyase activity by 96%, indicating the —SH group(s) is essential for the enzymatic activity.

In immunological tests of the lyase by Western blotting, the results showed that the antibodies to the algal lyase could recognize the fungal lyase (of our earlier PCT patent application PCT/EP94/03397) both in cell-free extracts and in purified form, as revealed by Western blottings. The antibodies to the algal lyase purified form the algae collected in China (of our earlier PCT patent application PCT/EP94/03397) also recognized the lyase from the algae collected in Santa Cruz, Calif.

Further aspects and experiments relating to the enzyme according to the present invention will now be described.

THE SOLUBLE ENZYME SYSTEM

1. Effect of pH on the stability and activity of the lyase isolated from *Gracilariopsis lemaneformis*.

Two buffer systems, namely HOAc and NaOAc and sodium citrate—citric acid in a concentration of 5 mM—were tested at 37° C. The pH range tested was from pH 3 to pH 5.2. The lyase showed maximum activity in a pH range between 3.6 to 4.2. At pH 3, the stability and activity of the enzyme decreased by about 90%. At pH 5.2, the activity decreased by about 64%. However, the enzyme was considerably more stable at this pH than at pH 3, as the AF yield obtained at pH 5.2 was 75% of the AF yield obtained at pH 3.8. Slightly higher AF yield was obtained in the HOAc and NaOAc buffer than in citrate buffer. This is not due to any differential effect of the two buffers (final conc. is 125 $\mu$M in the AF assay mixture) in the AF assay method.

2. Effect of temperature on the activity and stability of the lyase.

This experiment was conducted at optimal pH range. At 25° C. the production of AF was linear up to at least 9 days. This indicates that no loss of activity and stability of the lyase occurred within 9 days. With increasing temperature, the stability of the enzyme decreased.

The half life of the enzyme activity at the following temperature was:

| | |
|---|---|
| 30° C. | 5 days |
| 37° C. | 2.5 days |
| 40° C. | less than 1 day |
| 50° C. | less than 1 day |

3. Effect of substrate concentration on the stability of the lyase and AF yield.

It was observed that amylopectin and dextrins have a stabilizing effect on the lyase while the smallest substrate maltose does not. This was verified for both the soluble enzyme system and the immobilized enzyme system.

AF yield increases with the increase in amylopectin concentration up to 25%. In the case of dextrin, the AF yield decreases when the concentration exceeds 30% (30%, 40% and 50% were tested).

4. Activation and inactivation of lyase

No metal ions were found to be necessary for the activity and the enzyme catalysed reaction can surprisingly proceed in pure water. The fact that the addition of EDTA in the reaction mixture up to 20 mM had little effect on the activity clearly demonstrates that metal ions are not essential for the activity of the lyase enzyme according to the present invention.

This means that in the AF purification step, the ion exchange chromatography step that takes away salts from the reaction system can be omitted, if water is used as reaction medium. However, inclusion of NaCl in the reaction mixture in a concentration of 0.85% (0.145 M) can increase the AF yield up to 1-fold.

5. Substrate Specificity

Upon cooling solubilized starch will tend to form rigid gets when the starch concentration becomes to high. Therefore it is an advantage to utilize partly degraded starch as substrate for the 1,4-glucan lyase.

The specificity of α-1,4-glucan lyase for different oligosaccharides was tested. The oligosaccharides were maltose (G2), maltotriose (G3), maltotetraose (G4), maltopentaose (G5), maltohexaose (G6) and maltoheptaose (G7). The oligosaccharides were dissolved in H$_2$O at a concentration of 8 mg/ml. The enzyme assay contained 150 $\mu$l substrate G2/G3/G4/G5/G6/G7, 120 $\mu$l 0.1M MES pH 6.3 and 30 $\mu$l purified enzyme. The reaction mixture was incubated for 60 min at 30° C. Afterwards the reaction was stopped by boiling for 3 min and 900 $\mu$l absolute ethanol was added for precipitation. After centrifugation at 20.000×g for 5 min at 4° C. the supernatant was transferred to a new eppendorf tube and lyophilized.

The freeze-dried samples were dissolved in 1000 $\mu$l H$_2$O and were filtrated through a 0.22 $\mu$m Millipore filter before 25 $\mu$l of the sample was loaded on the Dionex HPLC.

6. HPLC

Analyses were performed on a Dionex 4500i chromatography system consisting of a GPM-2 pump and a PED detector which was used in pulse-amperometric detection mode. The anion exchange columns were a CarboPac PA-100 (4×250 mm) and a CarboPac PA-100 guard column (3×25 mm) from Dionex. The eluent were 200 mM sodium hydroxide (A), 500 mM sodium acetate (B) and 18 M ohm de-ionized water (C). The pump was programmed in 2 different ways, method no. 1 and method no. 2:

| Method no. 1: | | | | | |
|---|---|---|---|---|---|
| Time, min | 0.0 | 3.0 | 3.1 | 26.9 | 29.0 |
| % A | 10 | 10 | 50 | 50 | 10 |
| % B | 0 | 0 | 0 | 32 | 0 |
| % C | 90 | 90 | 50 | 18 | 90 |

| Method no. 2: | | |
|---|---|---|
| Time, min. | 0.0 | 30 |
| % A | 10 | 10 |
| % B | 0 | 0 |
| % C | 90 | 90 |

Standards:

Glucose, maltose, maltotriose, maltotetraose, maltopentaose, maltohexaose and maltoheptaose (all from Sigma) and 1,5-anhydrofructose were used as standards. All compounds were dissolved in 18 M ohm de-ionized water which was filtered through a 0.22 $\mu$m Millipore filter before use.

7. Results

The analyses show that the purified enzyme was able to use maltooligosaccharides as substrate 1 for 1,5-anhydrofructose formation. When maltose was used as substrate, almost no 1,5-anhydrofructose was formed but when the other maltooligosaccharides (G3–G7) were used, high amounts of this compound were produced. It is clear that higher amounts of 1,5-anhydrofructose were obtained when a longer maltooligosaccharide was used. This observation corresponds perfectly well with the theory of the lyase forming 1,5-anhydrofructose from the non-reducing end of the substrate, leaving only the terminal glucose molecule unchanged.

8. Formation of AF

α-1,4-glucan lyase according to the present invention hydrolyses starch to the end-product 1,5-anhydrofructose. The end-product was shown by HPLC, method 2. The enzyme assay contained 500 $\mu$l amylopectin (20 mg/ml, dissolved in $H_2O$), 400 $\mu$l 0.1 M MES pH 6.3 and 100 $\mu$l purified enzyme. The reaction mixture was incubated at 30° C. and the reaction was stopped by boiling after 30 or 120 min incubation. High-molecular oligosaccharides were precipitated by addition of 3 vol abs. ethanol and the sample was centrifuged and freeze-dried as described above. The samples were dissolved in 125 $\mu$l $H_2O$ and 25 $\mu$l were applied on the HPLC column.

The HPLC elution profile clearly shows that α-1,4-glucan lyase produces 1,5-anhydrofructose by hydrolysis of starch. Equal amounts of 1,5-anhydrofructose were found after 30 and 120 min. incubation which indicate that the enzyme activity is not inhibited by the end-product 1,5-anhydrofructose.

$^{13}C$ NMR spectra (water) of AF prepared in this way shows that it adopts one major form giving rise to the following signals: δ 93.5 (quart, C-2), 81.5 (CH, C-5), 77.7 (CH, C-3), 72.6 ($CH_2$, C-1), 69,8 (CH, C-4), 62.0 ($CH_2$, C-6). Assignments are based on H—H C—H and C—H 2D correlation spectra.

9. The cooperative effect of lyase with pullulanase and isoamylase.

As it can be seen from the Table below, the inclusion of pullulanase in the reaction mixture will obviously increase the AF yield by about 15–23%, depending on whether soluble starch or amylopectin is used as substrate.

The cooperation of pullulanase and lyase in the production of AF.

| Substrate | Lyase | Pullulanase | AF Yield (%) | Glc Yield (%) |
|---|---|---|---|---|
| Solubl. | + | − | 51 | 0 |
| Starch | − | + | 0 | 0.37 |
|  | + | + | 66.0 | 3.9 |
| Amylo- | + | − | 48.0 | 0 |
| pectin | − | + | 0 | 0.33 |
|  | + | + | 71.3 | 3.7 |

+, enzyme added, − enzyme omitted.

The reaction mixture contained 0.3 ml 2% potato amylopectin (Sigma) in water or 0.3 ml 2% soluble starch (Merck), 2 $\mu$l lyase and 0.36 units pullulanase (BM) as indicated.

The reaction was carried out at 30° C. for 1 day. At the end of the reaction, samples were taken for AF and Glc analysis.

In the case of isoamylase, the advantage is that the optimal pH of the lyase overlaps with that of *Pseudomonas isoamylase* (pH 3.0–4.5). The problem, however, is that isoamylase will produce an excess amount of long chain amylose that precipitates from the solution, and therefore is no longer suitable as a substrate for the lyase. It can be expected that the cooperation of the lyase with isoamylase will be efficient, if the chain of amylose is not too long.

THE IMMOBILIZED ENZYME SYSTEM

Immobilization of the lyase was achieved by using succinimide-activated Sepharose (Affigel 15 gel, Bio-Rad) and glutaradehye-activated Silica gel (BM). The recovery of lyase activity after immobilization on Affigel 15 gel was between 40% to 50%. There may be some lyase that is still active after immobilization, but is inaccessible to the substrate because of the steric hindrance, especially in the case of macromolecules like starches. Immobilized enzymes used in the industry usually have an activity recovery of around 50%.

The most interesting thing of the Affigel 15 gel immobilized lyase is that its stability has been greatly improved at pH 5.5. When the column was operated at this pH, the stability was at least 16 days long. The Ph shift in the stability is very important considering the optimal pH of pullulanase which is around pH 5.5. This is the prerequisite for the lyase and pullulanase to cooperate efficiently in the same reactor with the same physico-chemical environment. The soluble lyase has an optimal pH between 3.6 and 4.2, and at this pH range pullulanase shows little or no activity.

With the silica gel immobilized lyase, the activity recovery is very high, around 80–100%. However, the silica gel immobilized enzyme was not stable when the column was operated neither at pH 3.8 nor pH 5.5. It is possible that some lyase was adsorbed on the surface of the silica gel beads and was slowly released from the silica gel after each washing of the column. It may therefore be the adsorbed lyase that contributes to the high recovery rate and the decrease in column activity.

PURIFICATION OF AF

1. The lyase-Amylopectin/Soluble Starch System

In this system, the reaction system contained AF, limit dextrin, the lyase, and buffer salts at the end of the reaction. AF was separated from the macromolecules (limit dextrin and the lyase) by ethanol (final conc. 50%) precipitation. Unprecipitated low-molecular-weight amylopectin was separated by ultrafiltration using Amicon YM3 membranes (cut-off 3,000). Ethanol was removed by evaporation at 40° C. in a rotary evaporator. Buffer salts were removed from AF by mixed ion exchangers. Purified solid AF was obtained by freeze-drying.

2. The Lyase-Pullulanase/Amylopectin/Soluble Starch System.

In this system the final products are AF and glucose. If at least a substantially pure sample of AF is to be prepared, the by-product glucose must be removed. This can be achieved by enzymatic methods. First the glucose is converted into gluconic acid and hydrogen peroxide by glucose oxidase. Catalase is needed to dispel $H_2O_2$ formed. $H_2O_2$ will oxidize AF into two new compounds which are at present of unknown structure. The other impurities in the AF preparation are the oxidation products of AF. It was observed that AF can slowly be oxidized by air-level of oxygen, especially at high temperature, high AF concentration and long time of exposure. Gluconic acid was removed together with the buffer salts by ion exchange chromatography.

In this system, the low-molecular-weight amylopectin molecules may alternatively be hydrolysed by amyloglucosidase instead of using ultrafiltration.

3. The purity checking of AF.

The purity of the AF preparations were confirmed by TLC, Dionex and NMR.

4. Analysis of the antioxidative activity of anhydro fructose.

Electrochemical oxygen consumption:

The activity of AF was investigated in a methyl linoleate emulsion as described by Jorgensen and Skibsted (Z. Lebensm. Unters. Forsch. (1993) 196: 423–429) with minor modifications: To 5.00 ml of a 1.33 mM methyl linoleate emulsion in 5.0 mM aqueous phosphate buffer with pH=5.8 and 0.2 w/w % Tween 20 as emulsifier was added AF in the following concentrations: 0, 15, 146 and 680 $\mu$M. The oxidation in the system was initiated by addition of 50 $\mu$l 0.26 M metmyoglobin (MMb) final concentration 0.26 mM. Immediately after initiating the reaction the sample was injected to a thermostated (25.0±0.1° C.) 70 $\mu$l closed cell, effectively excluding diffusion of oxygen into the system. The oxygen consumption was measured by a Clark electrode, which was connected to a PC data collection program. The relative oxygen concentration (%) was registered every 30 s.

The results of the experiments produced curves corresponding to oxygen consumption. For samples without addition of AF a relative decrease in oxygen concentration is seen immediately after injection of the sample. For samples containing AF a lag-phase is observed before the curve breaks off and the oxygen concentration is reduced. After the lag-phase only a minor reduction in the oxygen consumption rate is observed compared to samples without AF added. A tendency for samples having the highest amount of AF to have the longest lag-phase is observed. Also, the rate for oxygen consumption is lower for these samples, which was seen by the smaller slope of the curves compared to the slope for the references (0 $\mu$M).

ESR analysis:

Hydroxyl radicals were generated by a Fenton reaction with $H_2O_2$ (0.17 mM) and $FeSO_4$ (4.8 $\mu$M). The generated radicals were trapped by 5,5-dimethyl-1-pyrroline N-oxide (DMPO, 9.7 mM). AF was added in concentrations of 1.3 mM and 6.3 mM. A water soluble extract of rosemary (*Rosmarinus officinalis* L.) was analyzed in a concentration of 0.25 mg/ml (in grams equivalent to 1.26 mM AF). Measurements were carried out at room temperature (20±1° C.) after 120 s and repeated for the same reaction mixture after 300 s with the following spectrometer settings: Center field 3475.60 G; sweep width 55 G; microwave power 20 mW; modulation frequency 100 kHz; modulation amplitude 1.01 G; receiver gain 1.00·$10^5$; conversion time 81.92 ms time constant 163.84 ms and sweep time 83.89 s.

The results showed that the generated hydroxyl radicals were trapped by DMPO. The spin adduct gives rise to a characteristic 1:2:2:1 ESR spectrum. The peak height of the spectrum is proportional to the quantitative amount of generated spin adduct. Addition of both DMPO and AF will set up a competition between the spin trap and AF. A reduction of peak height will indicate a good scavenging activity of AF.

TABLE

Peak height of ESR-spectra. $H_2O_2$ = 0.17 mM and $Fe^{2+}$ = 4.8 $\mu$M.

| Anhydro fructose [mM] | Rosemary extract [mg/ml] | Peak height [120 s] | Peak height [300 s] |
|---|---|---|---|
| 0 | 0 | 2475 | 2780 |
| 1.3 | 0 | 2634 | 2545 |
| 6.3 | 0 | 1781 | 1900 |

At a concentration of 1.3 mM AF no scavenging activity of hydroxyl radicals is seen, at 6.3 mM Af the peak height is reduced, indicating that a part of the generated hydroxyl radicals is scavenged by AF.

USE OF AF AS AN ANTI-OXIDANT

1. Use of AF as an anti-oxidant in a 50% mayonnaise.

50% mayonnaise is used for salads, open sandwiches, etc. in both the catering and the retail trades. The low oil content of 50% mayonnaise makes it suitable for low-calorie applications.

A typical mayonnaise composition is as follows:

| | |
|---|---|
| Soya oil | 50.0% |
| Tarragon vinegar (10%) | 4.0% |
| Egg yolk | 3.5% |
| Sugar | 3.0% |
| Salt | 1.0% |
| Potassium sorbate | 0.1% |
| Water | 35.2% |
| MAYODAN 602 | 3.0% |
| Lemon flavouring 10251 | 0.2% |

MAYODAN 602 ensures a fine, stable oil dispersion and the required viscosity, thereby providing 50% mayonnaise with a long shelf life.

Flavouring 10251 is a natural lemon flavouring which provides mayonnaise with the fresh taste of lemon.

Typically the mayonnaise is prepared by the following method:

1) Dry mix the MAYODAN 602, sugar and salt. Disperse in oil in a ratio of 1 part powder to 2 parts oil.
2) Add flavouring and potassium sorbate to the water and pour into the Koruma mixer. Add 1).
3) Add the egg yolk.
4) Add the oil continuously in a vacuum.
5) After ⅔ of the oil has been added (slowly), blend the tarragon vinegar with the remaining ⅓ of the oil, and add.

The following data show that when AF is added to the mayonnaise as an anti-oxidant the results are comparable to the know food anti-oxidants GRINDOX 142 (antioxidant) and GRINDOX 1029 (antioxidant).

| | | |
|---|---|---|
| GRINDOX 142 (antioxidant). | | |
| | Ascorbyl palmitate | 10% |
| | Propyl gallate | 20% |
| | Citric acid | 10% |
| | Food grade emulsifier | 60% |
| | Form at 25° C. | paste |
| | Colour | grey to pale brown |
| | Density | 1.1 g/ml |
| GRINDOX 1029 (antioxidant). | | |
| | Ascorbyl palmitate | 20% |
| | Natural tocopherols | 20% |
| | Food grade emulsifier | 60% |
| | Form at 25° C. | paste |
| | Colour | light brown |
| | Density at 25° C. | 1,0 g/ml |

(All percentages are by weight)

In the test procedure the anti-oxidants were added to the mayonnaise to provide an anti-oxidant concentration in the order of about 500 ppm. The mayonnaise was then placed in a bomb calorimeter at temperature 80° C. containing pure $O_2$. An induction period to the onset of substantial oxidation of the product is then measured.

The results were as follows.

| Samples: | | IP (hours) |
|---|---|---|
| 1. | Blank | 28,0 |
| 2. | +500 ppm GRINDOX 142 | 35,0 |
| 3. | +500 ppm GRINDOX 1029 | 33,3 |
| 4. | +550 ppm GRINDOX 1029 | 34,3 |
| 5. | +500 ppm 1,5 anhydro-D-fructose | 32,0 |

(IP hours = Induction Period)

These results show that AF is an excellent food anti-oxidant and is comparable with the known foodstuffs anti-oxidants GRINDOX 142 or GRINDOX 1029.

2. Use of AF as an anti-oxidant in a salad dressing

YOGURT SALAD DRESSING WITH 50% OIL

Yogurt salad dressing with 50% oil is used for salads, potatoes, raw vegetable salad, meat, fish and boiled vegetables.

| Composition | |
|---|---|
| Soya oil | 50.0% |
| Yogurt (plain) | 39.0% |
| Vinegar (10%) | 3.5% |
| Sugar | 3.0% |
| Egg yolk | 2.0% |
| Salt | 1.0% |
| Potassium sorbate | 0.1% |
| MAYODAN 525 | 1.4% |
| Acid masking flavouring 2072 | 0.02% |

MAYODAN 525 (stabilizer blend) provides unique emulsion stability, prevents syneresis, ensures uniform oil dispersion and viscosity, improves tolerance to production processes and ensures a long shelf life.

Flavouring 2072 is a nature-identical, acid masking flavouring reducing the acidulated taste of dressing without affecting its pH value.

Method
1. Dry mix MAYODAN 525, sugar and salt. Disperse in oil in a ratio of 1 part powder to 2 parts oil.
2. Fill flavouring, potassium sorbate and yogurt into the Koruma mixer. Add 1).
3. Add the egg yolk.
4. Add the oil continuously in a vacuum.
5. After ⅔ of the oil has been added (slowly), blend the vinegar with the remaining ⅓ of the oil, and add.
6. Add spices if required.

Test results:

| Sample: | IP hours | PF |
|---|---|---|
| 1. Blank | 37.2 | 1.00 |
| 2. 500 ppm anhydrofructose | 39.5 | 1.06 |
| 3. 800 ppm GRINDOX 1032 | 43.3 | 1.07 |

(IP - Induction Period); (PF - Protection Period)

Protection Factor (PF):

For each temperature defined as PF=IP of the oil with added antioxidant/IP of the same oil without added antioxidant Life extension (LE) %:
LE=(PF−1.0)×100

FURTHER STUDIES

1. Effect of alcohols in increasing the activity and stability of the lyase purified from the algae.

1-propanol, 2-propanol and 1-butanol were tested at the following concentrations (0%, 1%, 5% and 10%). The optimal concentration of 1-propanol was 5% which increased the AF yield by 34% after 6 days of incubation; the optimal concentration for 2-propanol was 1% which increased the AF yield by 20% after 10 days incubation; the optimal concentration for 1-butanol was 5% which increased the AF yield by 52% after 3-day incubation.

Ethanol was tested at the following concentrations (0, 1, 3, 5, 7, 9, 11, 13, 15%). The optimal concentration for 7 days incubation was 5% which increased the AF yield by 12%. For 10 days incubation the optimal concentration was 3% which increased AF yield by 16%.

The effect of 1-propanol:

| 1-propanol concentration | Reaction time (days) | | | | |
|---|---|---|---|---|---|
| (v/v) | 0 | 1 | 3 | 6 | 10 |
| | AF yield ($\mu$mol) | | | | |
| 0% | 0 | 84 | 261 | 451 | 689 |
| 1% | 0 | 80 | 280 | 530 | 803 |
| 5% | 0 | 115 | 367 | 605 | 853 |
| 10% | 0 | 107 | 307 | 456 | 583 |

2. Effect of different reaction media upon the production of AF by the lyase purified from the algae The results (see table below) indicate that the best reaction medium is 5 mM of HOAc-NaOAc (pH 3.9) (BACE for short) and containing mM concentrations of $Na_2$-EDTA. The production of AF using either pure water or 0.85% NaCl as reaction medium decreased the yield. Inclusion of 0.85% of NaCl in BACE also decreased the AF yield.

| Reaction | Reaction Time (days) | | | |
|---|---|---|---|---|
| Media | 0 | 1 | 3 | 8 |
| | AF yield ($\mu$mol) | | | |
| BACE | 0 | 229 | 498 | 575 |
| Water | 0 | 46 | 128 | 217 |
| NaCl (0.85%) | 0 | 123 | 239 | 249 |
| BACE + NaCl (0.85%) | 0 | 153 | 281 | 303 |

The following buffers: Mes-NaOH, Mops-NaOH, Hepes-NaOH, and Bicine-NaOH were the optimal reaction media for the lyase.

3. The effect of endoamylases and debranching enzymes upon the AF production.

Endoamylase

The starch used for AF production may first be liquified either by endoamylases, or by acid hydrolysis.

Endoamylase degraded starch is more suitable as substrate for the lyase as compared to native starch. Starch has a limited solubility at the temperature used for the lyase-catalyzed reaction. Treatment of starch with endoamylases led to increased glucose yied. It was found that a reducing matter of around 10–15% (on a dry mater basis) was most suitable as substrate for the lyase with respect to AF yield and further treatment with the endoamylase to a reducing matter of 19% was no longer suitable for the lyase.

Pullulanase and isoamylase

As seen from the results below, both the isoamylase and the pullulanase increased AF yield by up to 50% at pH 4.5 and 5.0. The reaction system consisted of the lyase from the algae with or without the addition of isoamylase or pullulanase (MegaZyme Ltd.). Amylopectin was used as substrate. The AF produced in the presence of only the lyase was expressed as 100%.

| | The pH of the reaction medium | | |
|---|---|---|---|
| Enzymes added | 3.5 | 4.5 | 5.0 |
| Lyase only | 100 | 100 | 100 |
| Lyase + isoamylase | 136 | 152 | 150 |
| Lyase + pullulanase | 132 | 158 | 155 |

4. Reversible and Irreversible Inhibitors of the lyase

The reversible inhibitors, Glucose and Maltose.

At a substrate concentration of 10 mg/ml, the activity for the lyase decreased by 19.3% in the presence of 0.1 M glucose when amylopectin was used as substrate; the activity was not affected when glycogen was used as substrate. In the presence of 0.1 M of maltose the activity decreased by 48.8% and 73.4%, respectively for glycogen and amylopectin.

| Substrates | Inhibitors | |
|---|---|---|
| Concentrations | Glucose | Maltose |
| Amylopectin 1% (2%) | 19.3% (7%) | 73.4% (67.2%) |
| Glycogen 1% (2%) | 0.000 (-) | 48.8% (49.7%) |

It seems that the inhibition by 0.1 M glucose is competitive as increasing the substrate from 1% to 2% decreased the inhibition from 19.3 to 7%, whereas the inhibition by 0.1 M maltose is non-competitive as the increase of substrate did not significantly affect the inhibition degree.

| Substrates | Glucose | Maltose |
|---|---|---|
| Amylopectin (1%) | 28% | 80% |
| Glycogen (1%) | 5% | 57% |

The reversible inhibitor deoxyjirimycin

At a final substrate concentration of 2%, the activity was decreased to 10.4% for the algal lyase in the presence of 25 $\mu$M of deoxyjirimycin, using amylopectin as substrate. At 100 $\mu$M, the activity of the lyase was completely lost.

Irreversible Inhibitor: PCMB

Under the same assay conditions and in the presence of 2 mM PCMB, the activity decreased by 60% for the lyase.

SCALE PRODUCTION OF AF

1. Production of AF using dextrin as substrate

The reactor contained 1000 g dextrins (obtained by treatment of starch with Termamyl to a final reducing matter of 10%) in a final volume of 4.6 liter (HOAC-NaOAC, pH 3.9, containing 5 mM $Na_2$-EDTA). The reaction was initiated by adding 3 mg purified lyase. The reaction was performed at room temperature. At day 19, another batch of lyase (4 mg) was added.

| Reaction time (days) | | | | | | |
|---|---|---|---|---|---|---|
| 0 | 1 | 7 | 13 | 19 | 24 | 31 |
| | | | AF produced (grams) | | | |
| 0 | 18 | 116 | 195 | 264 | 500 | 668 |

2. Using $^{14}C$-Starch for the production of $^{14}C$-AF

The uniformly labelled $^{14}C$-starch (340 $\mu$Ci obtained from Sigma) was vacuum-dried to remove the ethanol it contained and then dissolved in 2 ml water. The reaction was initiated by adding 20 $\mu$l purified lyase and 20 $\mu$l pullulanase (MegaZyme Ltd.) The reaction was performed overnight at 30° C. At the end of the reaction, the reaction mixture was filtered using a filter with a molecular mass cut off of 10,000 to remove the enzymes and unreacted starch molecules.

The filtrate was applied on a $Ca_2$ carbohydrate column (CHROMPACK (gas chromatography and liquid chromatography instruments and supplies)) using a Waters HPLC. Water was used as eluent. The flow rate was 0.5 ml/min. AF was efficiently separated from glucose and maltosaccharides. The pooled AF fractions were freeze-dried and totally 140 $\mu$Ci $^{14}C$-AF was obtained.

These findings relate to an even further aspect of the present invention, namely the use of a reagent that can increase the hydrophobicity of the reaction medium (preferably an alcohol) to increase the stability and activity of the lyase according to the present invention. This increased stability leads to a increased AF yield.

Other modifications of the present invention will be apparent to those skilled in the art without departing from the scope of the invention.

[GRINDOX (antioxidant) as used herein is a trade mark. MAYODAN (stabilizer blend) as used herein is a trade mark.]

What is claimed is:

1. An enzyme comprising (a) the amino acid sequence of SEQ ID NO: 3 or SEQ ID NO:4, (b) an amino acid sequence which is at least 85% homologous to the amino acid sequence of SEQ ID NO:3 or SEQ ID NO:4 wherein said enzyme has α-1,4 glucan lyase activity.

2. An isolated enzyme according to claim 1, wherein said enzyme possesses the following characteristics:

i) the enzyme can convert α-1,4-glucan to 1,5-D-anhydrofructose;
   ii) the enzyme can convert amylopectin, amylose, and dextrin to 1,5-D-anhydrofructose and glucose;
   iii) the enzyme can maintain enzymatic activity in pure water;
   iv) the enzyme can maintain enzymatic activity for at least one year at 4° C.

3. An isolated enzyme according to claim 2, which comprises the amino acid sequence of SEQ ID NO:3 OR SEQ ID NO:4.

4. An isolated enzyme according to claim 2, which is isolated from algae.

5. An isolated enzyme according to claim 4, wherein the algae is *Gracilariopsis lemaneiformis*.

6. An isolated enzyme according to claim 4, which is isolated by cyclodextrin affinity chromatography.

7. An isolated enzyme according to claim 2, which has been recombinantly produced by expressing the polynucleotide sequence of SEQ ID NO:1 or SEQ ID NO:2.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 3279 base pairs
      (B) TYPE: nucleic acid
      (C) STRANDEDNESS: double (D) TOPOLOGY: linear (ii) MOLECULE TYPE: Genomic DNA (xi) SEQUENCE DESCRIPTION: SEQ ID NO:1:

```
ATGTTTCCTA CCCTGACCTT CATAGCGCCC AGCGCGCTGG CCGCCAGCAC CTTTGTGGGC     60
GCGGATATCC GATCGGGCAT TCGCATTCAA TCCGCTCTTC CGGCCGTGCG CAACGCTGTG    120
CGCAGGAGCA AACATTACAA TGTATCCATG ACCGCATTGT CTGACAAGCA AACCGCTATC    180
AGTATTGGCC CTGACAATCC GGACGGTATC AACTACCAAA ACTACGATTA CATCCCTGTA    240
GCGGGCTTTA CGCCCCTCTC CAACACCAAC TGGTATGCTG CCGGCTCTTC CACTCCGGGC    300
GGCATCACCG ACTGGACCGC TACCATGAAT GTCAAATTCG ACCGCATTGA CAATCCGTCG    360
TACTCCAATA ACCATCCTGT TCAGATTCAG GTCACGTCGT ACAACAACAA CAGCTTCAGG    420
ATTCGCTTCA ACCCTGATGG CCCCATTCGT GACGTCTCTC GAGGACCTAT CCTGAAACAG    480
CAACTCACTT GGATTCGAAA CCAGGAGCTG GCGCAGGGAT GTAATCCGAA CATGAGCTTC    540
TCTCCTGAAG GTTTTTTGTC TTTTGAAACC AAAGACCTAA ACGTTATAAT CTACGGCAAC    600
TGCAAGATGA GAGTCACGAA GAAGGATGGC TACCTCGTCA TGGAGAATGA CGAGTGCAAC    660
TCGCAATCAG ATGGCAATAA GTGTAGAGGA TTGATGTACG TTGACCGGCT ATACGGTAAT    720
GCTATTGCTT CCGTACAAAC GAATTTTCAC AAAGACACTT CTCGGAACGA GAAATTCTAT    780
GGTGCAGGTG AAGTCAACTG TCGCTATGAG GAGCAGGGTA AGGCGCCGAC TTATGTTCTA    840
GAACGCTCTG GACTCGCCAT GACCAATTAC AATTACGACA ACTTGAACTA CAACCAACCA    900
GACGTCGTTC CTCCAGGTTA TCCCGACCAT CCCAACTACT ACATTCAAT GTACTACGCA     960
GCACCGTGGT TGGTCGTTCA GGGATGCGCG GGACATCGA AGCAATACTC GTACGGTTGG    1020
TTTATGGACA ATGTCTCTCA GTCGTACATG AACACTGGAG ATACGGCGTG GAACTGCGGA    1080
CAGGAAAACC TGGCATACAT GGGCGCGCAA TACGGGCCAT TGATCAGCA CTTTGTGTAT    1140
GGTGATGGAG ATGGCCTTGA AGATGTCGTC AAAGCGTTCT CCTTTCTTCA AGGAAAGGAG    1200
TTCGAAGACA AAAAACTCAA CAAGCGTTCT GTAATGCCTC CGAAGTACGT GTTTGGTTTC    1260
TTCCAGGGTG TTTTCGGTGC ACTTTCACTG TTGAAGCAGA ATCTGCCTGC CGGAGAGAAC    1320
AACATCTCAG TGCAAGAGAT TGTGGAGGGT TACCAGGATA CGACTACCC CTTTGAAGGG    1380
CTCGCGGTAG ATGTTGATAT GCAAGATGAT CTGCGAGTGT TTACTACCAA ACCAGAATAT    1440
TGGTCGGCAA ACATGGTAGG CGAAGGCGGT GATCCTAATA ACAGATCAGT CTTTGAATGG    1500
GCACATGACA GGGGCCTTGT CTGTCAGACG AACGTAACTT GCTTCTTGAG GAACGATAAC    1560
AGTGGGAAAC CATACGAAGT GAATCAGACA TTGAGGGAGA ACAGTTGTA TACGAAGAAT    1620
GATTCCTTGA ACAACACCGA TTTTGGAACT ACCTCGGATG GGCCTGGCGA TGCGTACATT    1680
GGACATTTGG ACTATGGTGG TGGAGTGGAG TGTGATGCAA TCTTCCCAGA CTGGGGTCGA    1740
CCAGACGTGG CTCAATGGTG GGGAGAAAAC TACAAGAAGC TGTTCAGCAT TGGTCTCGAT    1800
TTCGTGTGGC AGGATATGAC GGTACCTGCG ATGATGCCGC ACCGACTCGG TGATGCTGTC    1860
AACAAAAATT CCGGTAGTTC GGCGCCGGGC TGGCCGAATG AGAACGATCC ATCCAACGGA    1920
CGATACAACT GGAAATCTTA TCATCCGCAA GTGCTCGTGA CCGACATGCG CTATGGTGCA    1980
GAGTATGGAA GGGAACCGAT GGTGTCTCAA CGCAACATTC ACGCCTACAC TCTTTGTGAA    2040
TCTACCAGAC GGGAGGGAAT TGTGGGAAAC GCAGACAGTT TGACCAAGTT CCGCCGCAGT    2100
TACATCATCA GTCGAGGAGG TTACATCGGT AACCAGCATT TCGGAGGGAT GTGGGTTGGG    2160
GACAACAGTG CCACAGAATC CTACCTCCAA ATGATGTTGG CGAACATTAT CAACATGAAT    2220
```

```
ATGTCGTGCC TCCCGCTAGT TGGCTCTGAT ATTGGCGGGT TCACCCAGTA CAATGATGCG   2280

GGCGACCCAA CCCCCGAGGA TTTGATGGTA AGATTCGTGC AGGCTGGCTG TCTGCTACCG   2340

TGGTTCAGAA ACCACTATGA CAGGTGGATT GAGTCCAAGA AGCACGGGAA GAAATACCAG   2400

GAGTTATACA TGTACCCGGG GCAAAAGGAT ACGTTGAAGA AGTTCGTTGA ATTCCGCTAC   2460

CGCTGGCAGG AGGTTTTGTA CACAGCCATG TACCAAAATG CTACCACTGG AGAGCCGATC   2520

ATCAAGGCGG CGCCCATGTA CAACAACGAC GTCAACGTGT ATAAATCGCA GAATGATCAT   2580

TTCCTTCTCG GTGGACATGA CGGCTATCGT ATTCTCTGCG CACCTGTTGT GCGCGAAAAT   2640

GCGACAAGTC GCGAAGTGTA CCTGCCTGTG TATAGCAAGT GGTTCAAATT CGGACCGGAC   2700

TTTGACACTA AGCCCTTGGA AAATGAGATT CAAGGAGGTC AGACGCTTTA TAATTACGCT   2760

GCACCGCTGA ACGATTCGCC GATATTTGTG AGGGAAGGGA CTATTCTTCC GACACGGTAC   2820

ACGCTGGACG GTGTGAACAA ATCTATCAAC ACGTACACAG ACAATGATCC GCTTGTATTT   2880

GAGCTGTTCC CTCTCGAAAA CAACCAGGCG CATGGCTTGT TCTATCATGA TGATGGCGGT   2940

GTCACCACCA ACGCTGAAGA CTTTGGCAAG TATTCTGTGA TCAGTGTGAA GGCCGCGCAG   3000

GAAGGTTCTC AAATGAGTGT CAAGTTTGAC AATGAAGTTT ATGAACACCA ATGGGGAGCA   3060

TCGTTCTATG TTCGTGTTCG TAATATGGGT GCTCCGTCTA ACATCAACGT ATCTTCTCAG   3120

ATTGGTCAAC AGGACATGCA ACAGAGCTCC GTGAGTTCCA GGGCGCAAAT GTTCACTAGT   3180

GCTAACGATG GCGAGTACTG GGTTGACCAG AGCACGAACT CGTTGTGGCT CAAGTTGCCT   3240

GGTGCAGTTA TCCAAGACGC TGCGATCACT GTTCGTTGA                          3279

(2) INFORMATION FOR SEQ ID NO:2:

(i) SEQUENCE CHARACTERISTICS:
        (A) LENGTH: 1712 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:2:

ATGACAAACT ATAATTATGA CAATTTGAAC TACAATCAAC CGGACCTCAT CCCACCTGGC    60

CATGATTCAG ATCCTGACTA CTATATTCCG ATGTACTTTG CGGCACCATG GGTGATCGCA   120

CATGGATATC GTGGCACCAG CGACCAGTAC TCTTATGGAT GGTTTTTGGA CAATGTATCC   180

CAGTCCTACA CAAACACTGG CGATGATGCA TGGGCTGGTC AGAAGGATTT GGCGTACATG   240

GGGGCACAAT GTGGGCCTTT CGATCAACAT TTTGTGTATG AGGCTGGAGA TGGACTTGAA   300

GACGTTGTGA CCGCATTCTC TTATTTGCAA GGCAAGGAAT ATGAGAACCA GGGACTGAAT   360

ATACGTTCTG CAATGCCTCC GAAGTACGTT TTCGGATTTT TCCAAGGCGT ATTCGGAGCC   420

ACATCGCTGC TAAGGGACAA CTTACCTGCC GGCGAGAACA ACGTCTCTTT GGAAGAAATT   480

GTTGAAGGAT ATCAAAATCA GAACGTGCCA TTTGAAGGTC TTGCTGTGGA TGTTGATATG   540

CAAGATGACT TGAGAGTGTT CACTACGAGA CCAGCGTTTT GGACGGCAAA CAAGGTGGGG   600

GAAGGCGGTG ATCCAAACAA CAAGTCAGTG TTTGAGTGGG CACATGACAG GGGCCTTGTC   660

TGCCAGACGA ATGTAACTTG CTTCTTGAAG AACGAGAAAA ATCCTTACGA AGTGAATCAG   720

TCATTGAGGG AGAAGCAGTT GTATACGAAG AGTGATTCCT TGGACAACAT TGATTTTGGA   780

ACTACTCCAG ATGGGCCTAG CGATGCGTAC ATTGGACACT TAGACTACGG TGGTGGTGTG   840

GAGTGTGATG CACTATTCCC AGACTGGGGT CGACCAGACG TGGCTCAATG GTGGGGCGAT   900
```

```
AACTACAAGA AACTATTCAG CATTGGTCTC GATTTCGTCT GGCAAGATAT GACGGTACCT    960

GCGATGATGC CGCACCGACT CGGTGACCCT GTCGGCACAA ATTCCGGTGA GACGGCGCCG   1020

GGCTGGCCGA ATGATAAGGA TCCATCCAAC GGACGATACA ATTGGAAGTC TTACCATCCG   1080

CAAGTGCTCG TGACTGACAT GAGGTATGAC GATTACGGAA GAGATCCCAT TGTTACGCAA   1140

CGCAATCTCC ATGCCTACAC TCTTTGTGAG TCTACTAGGA GGGAAGGCAT TGTTGGAAAC   1200

GCAGATAGTC TGACGAAGTT CCGCCGCAGC TATATTATCA GTCGTGGAGG CTACATCGGT   1260

AATCAGCACT TTGGTGGGAT GTGGGTAGGA GACAACTCTT CTACGGAAGA CTACCTCGCA   1320

ATGATGGTTA TCAACGTTAT CAACATGAAC ATGTCCGGTG TCCCGCTCGT TGGTTCCGAT   1380

ATTGGAGGTT TCACGGAGCA TGACAAGAGA AACCCTTGCA CACCGGACTT GATGATGAGA   1440

TTTGTGCAGG CTGGATGCTT GCTACCGTGG TTCAGGAACC ACTACGATAG GTGGATCGAG   1500

AGCAAGAAAC ACGGAAAGAA CTACCAAGAG TTGTACATGT ACCGCGACCA CTTGGACGCC   1560

TTGAGAAGTT TTGTGGAACT CCGCTATCGC TGGCAGGAAG TGTTATACAC AGCCATGTAT   1620

CAGAATGCTT TGAACGGGAA GCCGATCATC AAAACGGTCT CCATGTACAA CAACGATATG   1680

AACGTCAAAG ATGCTCAGAA TGACCACTTC CT                                 1712

(2) INFORMATION FOR SEQ ID NO:3:

(i) SEQUENCE CHARACTERISTICS:
        (A) LENGTH: 1092 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Phe Pro Thr Leu Thr Phe Ile Ala Pro Ser Ala Leu Ala Ala Ser
 1               5                  10                  15

Thr Phe Val Gly Ala Asp Ile Arg Ser Gly Ile Arg Ile Gln Ser Ala
                20                  25                  30

Leu Pro Ala Val Arg Asn Ala Val Arg Arg Ser Lys His Tyr Asn Val
            35                  40                  45

Ser Met Thr Ala Leu Ser Asp Lys Gln Thr Ala Ile Ser Ile Gly Pro
        50                  55                  60

Asp Asn Pro Asp Gly Ile Asn Tyr Gln Asn Tyr Asp Tyr Ile Pro Val
65                  70                  75                  80

Ala Gly Phe Thr Pro Leu Ser Asn Thr Asn Trp Tyr Ala Ala Gly Ser
                85                  90                  95

Ser Thr Pro Gly Gly Ile Thr Asp Trp Thr Ala Thr Met Asn Val Lys
            100                 105                 110

Phe Asp Arg Ile Asp Asn Pro Ser Tyr Ser Asn Asn His Pro Val Gln
        115                 120                 125

Ile Gln Val Thr Ser Tyr Asn Asn Asn Ser Phe Arg Ile Arg Phe Asn
    130                 135                 140

Pro Asp Gly Pro Ile Arg Asp Val Ser Arg Gly Pro Ile Leu Lys Gln
145                 150                 155                 160

Gln Leu Thr Trp Ile Arg Asn Gln Glu Leu Ala Gln Gly Cys Asn Pro
                165                 170                 175

Asn Met Ser Phe Ser Pro Glu Gly Phe Leu Ser Phe Glu Thr Lys Asp
            180                 185                 190

Leu Asn Val Ile Ile Tyr Gly Asn Cys Lys Met Arg Val Thr Lys Lys
```

-continued

```
            195                 200                 205
Asp Gly Tyr Leu Val Met Glu Asn Asp Glu Cys Asn Ser Gln Ser Asp
    210                 215                 220

Gly Asn Lys Cys Arg Gly Leu Met Tyr Val Asp Arg Leu Tyr Gly Asn
225                 230                 235                 240

Ala Ile Ala Ser Val Gln Thr Asn Phe His Lys Asp Thr Ser Arg Asn
                245                 250                 255

Glu Lys Phe Tyr Gly Ala Gly Glu Val Asn Cys Arg Tyr Glu Glu Gln
                260                 265                 270

Gly Lys Ala Pro Thr Tyr Val Leu Glu Arg Ser Gly Leu Ala Met Thr
                275                 280                 285

Asn Tyr Asn Tyr Asp Asn Leu Asn Tyr Asn Gln Pro Asp Val Val Pro
290                 295                 300

Pro Gly Tyr Pro Asp His Pro Asn Tyr Tyr Ile Pro Met Tyr Tyr Ala
305                 310                 315                 320

Ala Pro Trp Leu Val Val Gln Gly Cys Ala Gly Thr Ser Lys Gln Tyr
                325                 330                 335

Ser Tyr Gly Trp Phe Met Asp Asn Val Ser Gln Ser Tyr Met Asn Thr
                340                 345                 350

Gly Asp Thr Ala Trp Asn Cys Gly Gln Glu Asn Leu Ala Tyr Met Gly
                355                 360                 365

Ala Gln Tyr Gly Pro Phe Asp Gln His Phe Val Tyr Gly Asp Gly Asp
                370                 375                 380

Gly Leu Glu Asp Val Val Lys Ala Phe Ser Phe Leu Gln Gly Lys Glu
385                 390                 395                 400

Phe Glu Asp Lys Lys Leu Asn Lys Arg Ser Val Met Pro Pro Lys Tyr
                405                 410                 415

Val Phe Gly Phe Phe Gln Gly Val Phe Gly Ala Leu Ser Leu Leu Lys
                420                 425                 430

Gln Asn Leu Pro Ala Gly Glu Asn Asn Ile Ser Val Gln Glu Ile Val
                435                 440                 445

Glu Gly Tyr Gln Asp Asn Asp Tyr Pro Phe Glu Gly Leu Ala Val Asp
                450                 455                 460

Val Asp Met Gln Asp Asp Leu Arg Val Phe Thr Thr Lys Pro Glu Tyr
465                 470                 475                 480

Trp Ser Ala Asn Met Val Gly Glu Gly Gly Asp Pro Asn Asn Arg Ser
                485                 490                 495

Val Phe Glu Trp Ala His Asp Arg Gly Leu Val Cys Gln Thr Asn Val
                500                 505                 510

Thr Cys Phe Leu Arg Asn Asp Asn Ser Gly Lys Pro Tyr Glu Val Asn
                515                 520                 525

Gln Thr Leu Arg Glu Lys Gln Leu Tyr Thr Lys Asn Asp Ser Leu Asn
                530                 535                 540

Asn Thr Asp Phe Gly Thr Thr Ser Asp Gly Pro Gly Asp Ala Tyr Ile
545                 550                 555                 560

Gly His Leu Asp Tyr Gly Gly Val Glu Cys Asp Ala Ile Phe Pro
                565                 570                 575

Asp Trp Gly Arg Pro Asp Val Ala Gln Trp Trp Gly Glu Asn Tyr Lys
                580                 585                 590

Lys Leu Phe Ser Ile Gly Leu Asp Phe Val Trp Gln Asp Met Thr Val
                595                 600                 605

Pro Ala Met Met Pro His Arg Leu Gly Asp Ala Val Asn Lys Asn Ser
610                 615                 620
```

-continued

```
Gly Ser Ser Ala Pro Gly Trp Pro Asn Glu Asn Asp Pro Ser Asn Gly
625                 630                 635                 640

Arg Tyr Asn Trp Lys Ser Tyr His Pro Gln Val Leu Val Thr Asp Met
            645                 650                 655

Arg Tyr Gly Ala Glu Tyr Gly Arg Glu Pro Met Val Ser Gln Arg Asn
                660                 665                 670

Ile His Ala Tyr Thr Leu Cys Glu Ser Thr Arg Arg Glu Gly Ile Val
            675                 680                 685

Gly Asn Ala Asp Ser Leu Thr Lys Phe Arg Arg Ser Tyr Ile Ile Ser
690                 695                 700

Arg Gly Gly Tyr Ile Gly Asn Gln His Phe Gly Gly Met Trp Val Gly
705                 710                 715                 720

Asp Asn Ser Ala Thr Glu Ser Tyr Leu Gln Met Met Leu Ala Asn Ile
                725                 730                 735

Ile Asn Met Asn Met Ser Cys Leu Pro Leu Val Gly Ser Asp Ile Gly
            740                 745                 750

Gly Phe Thr Gln Tyr Asn Asp Ala Gly Asp Pro Thr Pro Glu Asp Leu
            755                 760                 765

Met Val Arg Phe Val Gln Ala Gly Cys Leu Leu Pro Trp Phe Arg Asn
770                 775                 780

His Tyr Asp Arg Trp Ile Glu Ser Lys Lys His Gly Lys Lys Tyr Gln
785                 790                 795                 800

Glu Leu Tyr Met Tyr Pro Gly Gln Lys Asp Thr Leu Lys Lys Phe Val
                805                 810                 815

Glu Phe Arg Tyr Arg Trp Gln Glu Val Leu Tyr Thr Ala Met Tyr Gln
                820                 825                 830

Asn Ala Thr Thr Gly Glu Pro Ile Ile Lys Ala Ala Pro Met Tyr Asn
            835                 840                 845

Asn Asp Val Asn Val Tyr Lys Ser Gln Asn Asp His Phe Leu Leu Gly
850                 855                 860

Gly His Asp Gly Tyr Arg Ile Leu Cys Ala Pro Val Val Arg Glu Asn
865                 870                 875                 880

Ala Thr Ser Arg Glu Val Tyr Leu Pro Val Tyr Ser Lys Trp Phe Lys
                885                 890                 895

Phe Gly Pro Asp Phe Asp Thr Lys Pro Leu Glu Asn Glu Ile Gln Gly
            900                 905                 910

Gly Gln Thr Leu Tyr Asn Tyr Ala Ala Pro Leu Asn Asp Ser Pro Ile
            915                 920                 925

Phe Val Arg Glu Gly Thr Ile Leu Pro Thr Arg Tyr Thr Leu Asp Gly
930                 935                 940

Val Asn Lys Ser Ile Asn Thr Tyr Thr Asp Asn Asp Pro Leu Val Phe
945                 950                 955                 960

Glu Leu Phe Pro Leu Glu Asn Asn Gln Ala His Gly Leu Phe Tyr His
                965                 970                 975

Asp Asp Gly Gly Val Thr Thr Asn Ala Glu Asp Phe Gly Lys Tyr Ser
            980                 985                 990

Val Ile Ser Val Lys Ala Ala Gln Glu Gly Ser Gln Met Ser Val Lys
            995                 1000                1005

Phe Asp Asn Glu Val Tyr Glu His Gln Trp Gly Ala Ser Phe Tyr Val
    1010                1015                1020

Arg Val Arg Asn Met Gly Ala Pro Ser Asn Ile Asn Val Ser Ser Gln
025                 1030                1035                1040
```

-continued

```
Ile Gly Gln Gln Asp Met Gln Gln Ser Ser Val Ser Ser Arg Ala Gln
            1045                1050                1055

Met Phe Thr Ser Ala Asn Asp Gly Glu Tyr Trp Val Asp Gln Ser Thr
        1060                1065                1070

Asn Ser Leu Trp Leu Lys Leu Pro Gly Ala Val Ile Gln Asp Ala Ala
    1075                1080                1085

Ile Thr Val Arg
    1090

(2) INFORMATION FOR SEQ ID NO:4:

(i) SEQUENCE CHARACTERISTICS:
        (A) LENGTH: 570 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Thr Asn Tyr Asn Tyr Asp Asn Leu Asn Tyr Asn Gln Pro Asp Leu
  1               5                  10                  15

Ile Pro Pro Gly His Asp Ser Asp Pro Asp Tyr Tyr Ile Pro Met Tyr
                 20                  25                  30

Phe Ala Ala Pro Trp Val Ile Ala His Gly Tyr Arg Gly Thr Ser Asp
         35                  40                  45

Gln Tyr Ser Tyr Gly Trp Phe Leu Asn Val Ser Gln Ser Tyr Thr
     50                  55                  60

Asn Thr Gly Asp Asp Ala Trp Ala Gly Gln Lys Asp Leu Ala Tyr Met
 65                  70                  75                  80

Gly Ala Gln Cys Gly Pro Phe Asp Gln His Phe Val Tyr Glu Ala Gly
                 85                  90                  95

Asp Gly Leu Glu Asp Val Val Thr Ala Phe Ser Tyr Leu Gln Gly Lys
            100                 105                 110

Glu Tyr Glu Asn Gln Gly Leu Asn Ile Arg Ser Ala Met Pro Pro Lys
        115                 120                 125

Tyr Val Phe Gly Phe Phe Gln Gly Val Phe Gly Ala Thr Ser Leu Leu
    130                 135                 140

Arg Asp Asn Leu Pro Ala Gly Glu Asn Val Ser Leu Glu Glu Ile
145                 150                 155                 160

Val Glu Gly Tyr Gln Asn Gln Asn Val Pro Phe Glu Gly Leu Ala Val
                165                 170                 175

Asp Val Asp Met Gln Asp Asp Leu Arg Val Phe Thr Thr Arg Pro Ala
            180                 185                 190

Phe Trp Thr Ala Asn Lys Val Gly Glu Gly Gly Asp Pro Asn Asn Lys
        195                 200                 205

Ser Val Phe Glu Trp Ala His Asp Arg Gly Leu Val Cys Gln Thr Asn
    210                 215                 220

Val Thr Cys Phe Leu Lys Asn Glu Lys Asn Pro Tyr Glu Val Asn Gln
225                 230                 235                 240

Ser Leu Arg Glu Lys Gln Leu Tyr Thr Lys Ser Asp Ser Leu Asp Asn
                245                 250                 255

Ile Asp Phe Gly Thr Thr Pro Asp Gly Pro Ser Asp Ala Tyr Ile Gly
            260                 265                 270

His Leu Asp Tyr Gly Gly Val Glu Cys Asp Ala Leu Phe Pro Asp
        275                 280                 285
```

```
Trp Gly Arg Pro Asp Val Ala Gln Trp Trp Gly Asp Asn Tyr Lys Lys
    290                 295                 300
Leu Phe Ser Ile Gly Leu Asp Phe Val Trp Gln Asp Met Thr Val Pro
305                 310                 315                 320
Ala Met Met Pro His Arg Leu Gly Asp Pro Val Gly Thr Asn Ser Gly
                325                 330                 335
Glu Thr Ala Pro Gly Trp Pro Asn Asp Lys Asp Pro Ser Asn Gly Arg
            340                 345                 350
Tyr Asn Trp Lys Ser Tyr His Pro Gln Val Leu Val Thr Asp Met Arg
        355                 360                 365
Tyr Asp Asp Tyr Gly Arg Asp Pro Ile Val Thr Gln Arg Asn Leu His
    370                 375                 380
Ala Tyr Thr Leu Cys Glu Ser Thr Arg Arg Glu Gly Ile Val Gly Asn
385                 390                 395                 400
Ala Asp Ser Leu Thr Lys Phe Arg Arg Ser Tyr Ile Ile Ser Arg Gly
                405                 410                 415
Gly Tyr Ile Gly Asn Gln His Phe Gly Gly Met Trp Val Gly Asp Asn
            420                 425                 430
Ser Ser Thr Glu Asp Tyr Leu Ala Met Met Val Ile Asn Val Ile Asn
        435                 440                 445
Met Asn Met Ser Gly Val Pro Leu Val Gly Ser Asp Ile Gly Gly Phe
    450                 455                 460
Thr Glu His Asp Lys Arg Asn Pro Cys Thr Pro Asp Leu Met Met Arg
465                 470                 475                 480
Phe Val Gln Ala Gly Cys Leu Leu Pro Trp Phe Arg Asn His Tyr Asp
                485                 490                 495
Arg Trp Ile Glu Ser Lys Lys His Gly Lys Asn Tyr Gln Glu Leu Tyr
            500                 505                 510
Met Tyr Arg Asp His Leu Asp Ala Leu Arg Ser Phe Val Glu Leu Arg
        515                 520                 525
Tyr Arg Trp Gln Glu Val Leu Tyr Thr Ala Met Tyr Gln Asn Ala Leu
    530                 535                 540
Asn Gly Lys Pro Ile Ile Lys Thr Val Ser Met Tyr Asn Asn Asp Met
545                 550                 555                 560
Asn Val Lys Asp Ala Gln Asn Asp His Phe
                565                 570

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:5:

ATGACNAAYT AYAAYTAYGA YAA                                      23

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:6:

RTGNGGCATC ATNGCNGGNA C                                        21
```

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:7:

GTCATRTCYT GCCANACRAA RTC                                        23

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:8:

GAYAAYCCNG AYGGNATHRA YTA                                        23

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

RGAKACATTR TCCAWAAACC A                                          21

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:10:

GTRGATGTKG ATATGCAASA WGA                                        23

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:11:

CCACATNCCN CCSAASTGYT GSTT                                     24

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

GTGAGTCTAC TAGGAGGGAA                                          20

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:13:

```
ASSAASTGST CSTTYTG                                                    17
```

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:14:

```
TTCCCAGAYT GGGGTCGACC                                                 20
```

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:15:

```
GTSAASTCNG GNCCSAA                                                    17
```

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:16:

```
GGTAGCGGTC CAGTCGGTGA TGCC                                            24
```

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:17:

```
AGAGCCGGCA GCATACCAGT TGGTGTTGG                                       29
```

(2) INFORMATION FOR SEQ ID NO:18:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:18:

```
GAAGGATCCG TCGACATCGA TAATACGACT GAATTCGGGA TTTTTTTTTT TTTTTTT        57
```

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

GACGGCTATC GTATTCTCTG C                                              21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:20:

TACCTGCCTG TGTATAGCAA G                                              21

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:21:

AAGGATCCGT CGACATCGAT AAT                                            23